(12) United States Patent
Clay et al.

(10) Patent No.: US 11,027,069 B2
(45) Date of Patent: Jun. 8, 2021

(54) DRUG DELIVERY DEVICE WITH RETAINING MEMBER

(71) Applicant: Warsaw Orthopedic, Inc., Warsaw, IN (US)

(72) Inventors: Danielle L. Clay, Collierville, TN (US); Jeffrey C. Marx, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 409 days.

(21) Appl. No.: 15/875,216

(22) Filed: Jan. 19, 2018

(65) Prior Publication Data

US 2018/0140777 A1 May 24, 2018

Related U.S. Application Data

(62) Division of application No. 14/517,311, filed on Oct. 17, 2014, now Pat. No. 9,901,684.

(Continued)

(51) Int. Cl.
*A61M 5/24* (2006.01)
*A61M 5/31* (2006.01)
*A61M 37/00* (2006.01)
*A61M 5/315* (2006.01)
*A61M 5/28* (2006.01)
*A61M 5/50* (2006.01)

(52) U.S. Cl.
CPC ........ *A61M 5/2459* (2013.01); *A61M 5/3135* (2013.01); *A61M 5/31501* (2013.01); *A61M 37/0069* (2013.01); *A61M 5/2455* (2013.01); *A61M 5/285* (2013.01); *A61M 5/3134* (2013.01); *A61M 5/504* (2013.01); *A61M 2005/2462* (2013.01); *A61M 2005/312* (2013.01)

(58) Field of Classification Search
CPC .............. A61M 5/3134; A61M 5/3135; A61M 5/31501; A61M 37/0069; A61M 5/315; A61M 5/3136; A61M 5/31511; A61M 5/31505; A61M 5/31515; A61M 5/504; A61M 5/285; A61M 5/2455; A61M 5/2459; A61M 200/2462; A61M 200/312
See application file for complete search history.

(56) References Cited

U.S. PATENT DOCUMENTS 4,105,030 A 8/1978 Kercso
4,451,253 A 5/1984 Harman
(Continued)

*Primary Examiner* — Tiffany Legette
(74) *Attorney, Agent, or Firm* — Sorell, Lenna & Schmidt, LLP

(57) ABSTRACT

A drug delivery device is provided for delivering a drug to a target tissue site. The drug delivery device comprises a body comprising a proximal end and a distal end and a chamber disposed therebetween. An upper portion is disposed about the proximal end of the body. A retaining member is disposed within a wall of the body and engageable with the chamber and a plunger is configured for disposal within the upper portion and the chamber. The upper portion is movable about the proximal end of the body to open the chamber such that the plunger is disposed within a passageway defined within the chamber, and movement of the plunger in a distal direction pushes the retaining member such that the drug moves out of the body. Methods are also disclosed.

20 Claims, 18 Drawing Sheets

Related U.S. Application Data

(60) Provisional application No. 61/892,357, filed on Oct. 17, 2013, provisional application No. 61/892,243, filed on Oct. 17, 2013.

(56) References Cited

U.S. PATENT DOCUMENTS

| | | |
|---|---|---|
| 4,900,304 A * | 2/1990 | Fujioka ............ A61M 37/0069 604/242 |
| 5,204,655 A | 4/1993 | Yajima et al. |
| 5,207,678 A | 5/1993 | Harms et al. |
| 5,212,162 A | 5/1993 | Missel et al. |
| 5,756,127 A | 5/1998 | Grisoni et al. |
| 6,203,813 B1 | 3/2001 | Gooberman |
| 6,471,688 B1 | 10/2002 | Harper et al. |
| 6,478,776 B1 | 11/2002 | Rosenman et al. |
| 6,530,934 B1 | 3/2003 | Jacobsen et al. |
| 6,735,475 B1 | 5/2004 | Whitehurst et al. |
| 6,971,998 B2 | 12/2005 | Rosenman et al. |
| 7,001,892 B1 | 2/2006 | Chmielewski et al. |
| 7,252,651 B2 | 8/2007 | Haider et al. |
| 2001/0043915 A1 | 11/2001 | Frey |
| 2003/0139706 A1 * | 7/2003 | Gray .................... A61M 5/315 604/199 |
| 2004/0015133 A1 | 1/2004 | Karim |
| 2004/0064193 A1 | 4/2004 | Evans et al. |
| 2004/0111118 A1 | 6/2004 | Hill et al. |
| 2004/0220545 A1 | 11/2004 | Heruth et al. |
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2005/0007843 A1 | 1/2005 | Choi et al. |
| 2005/0074481 A1 | 4/2005 | Brekke et al. |
| 2005/0137579 A1 | 6/2005 | Heruth et al. |
| 2005/0152949 A1 | 7/2005 | Hotchkiss et al. |
| 2005/0177118 A1 | 8/2005 | Hoganson et al. |
| 2005/0245906 A1 | 11/2005 | Makower et al. |
| 2005/0249775 A1 | 11/2005 | Falotico et al. |
| 2006/0046961 A1 | 3/2006 | McKay et al. |
| 2006/0253100 A1 | 11/2006 | Burright et al. |
| 2006/0264839 A1 | 11/2006 | Veasey et al. |
| 2007/0055378 A1 | 3/2007 | Ankney et al. |
| 2007/0219564 A1 | 9/2007 | Rue et al. |
| 2008/0228193 A1 | 9/2008 | Matityahu |
| 2010/0106137 A1 * | 4/2010 | Simonton .......... A61B 17/3468 604/511 |
| 2011/0040245 A1 * | 2/2011 | Garcia De Castro Andrews ........ A61M 37/0069 604/60 |

* cited by examiner

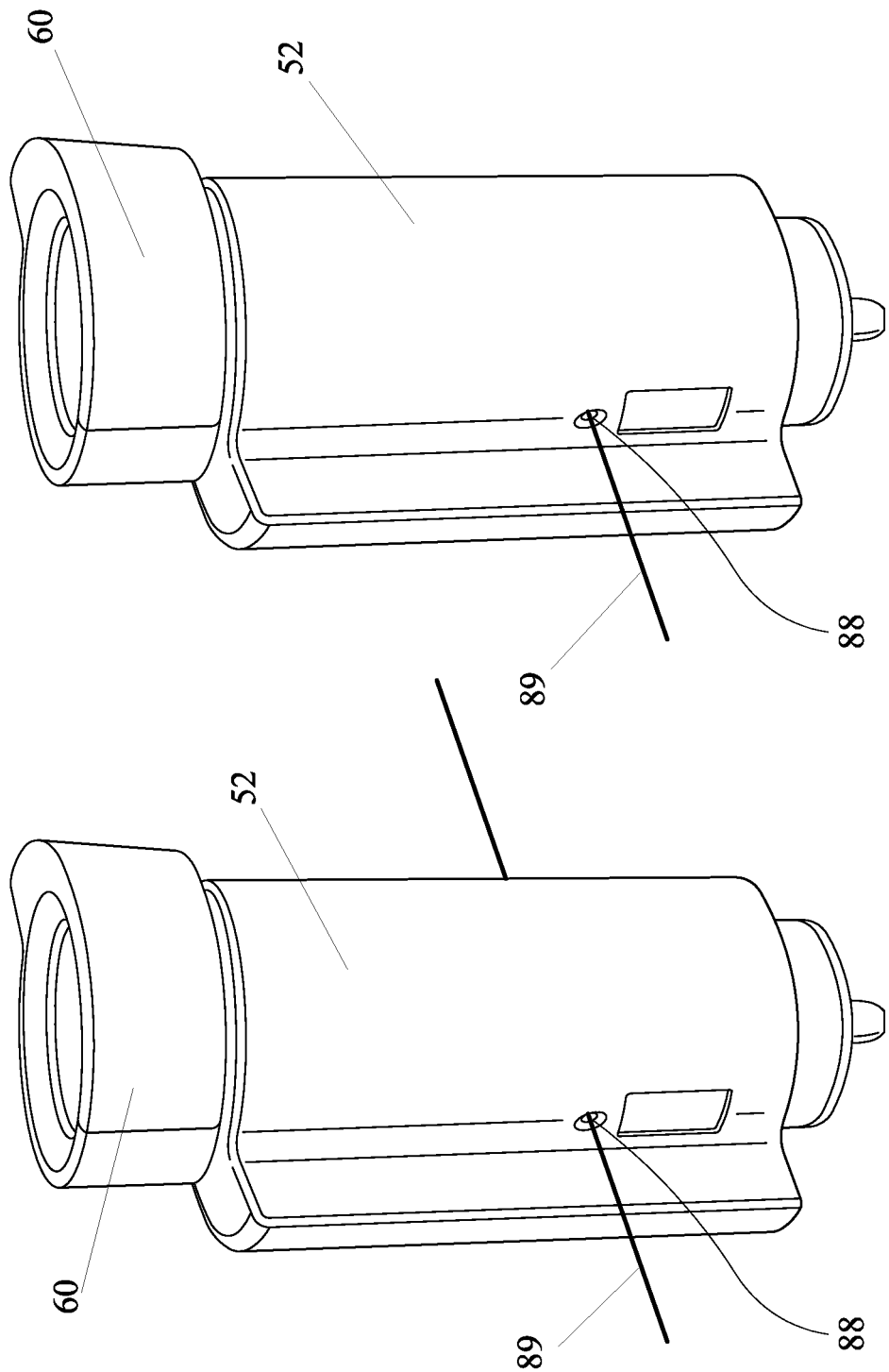

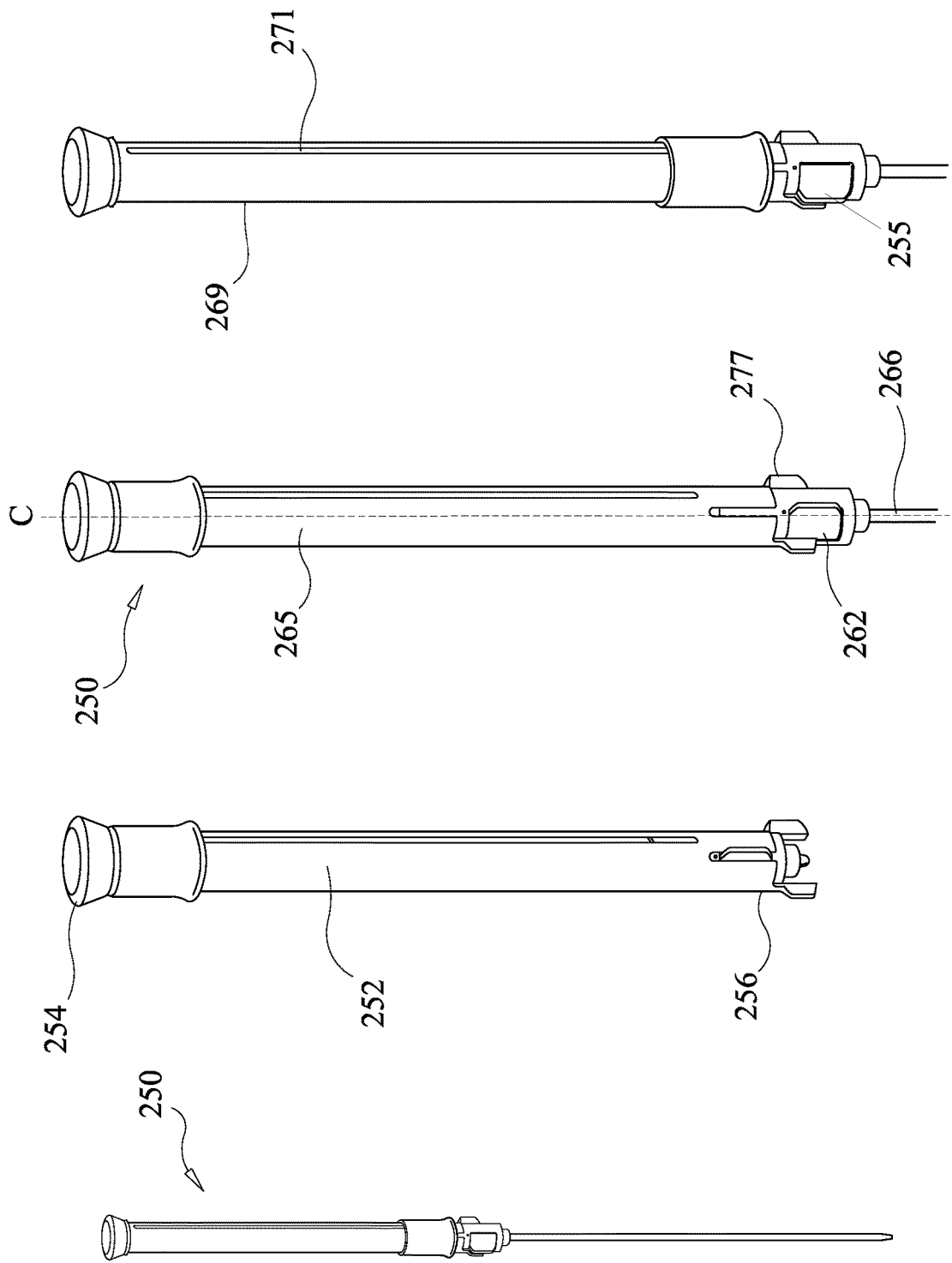

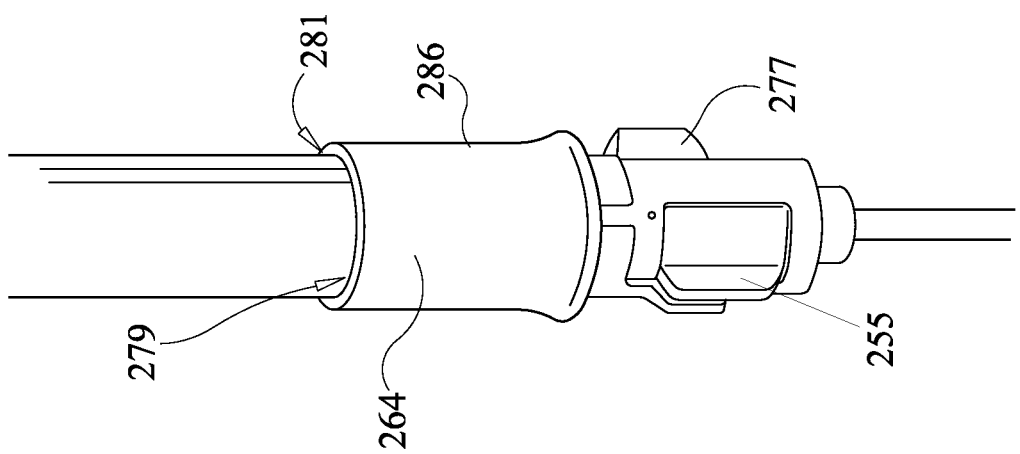
FIG. 28
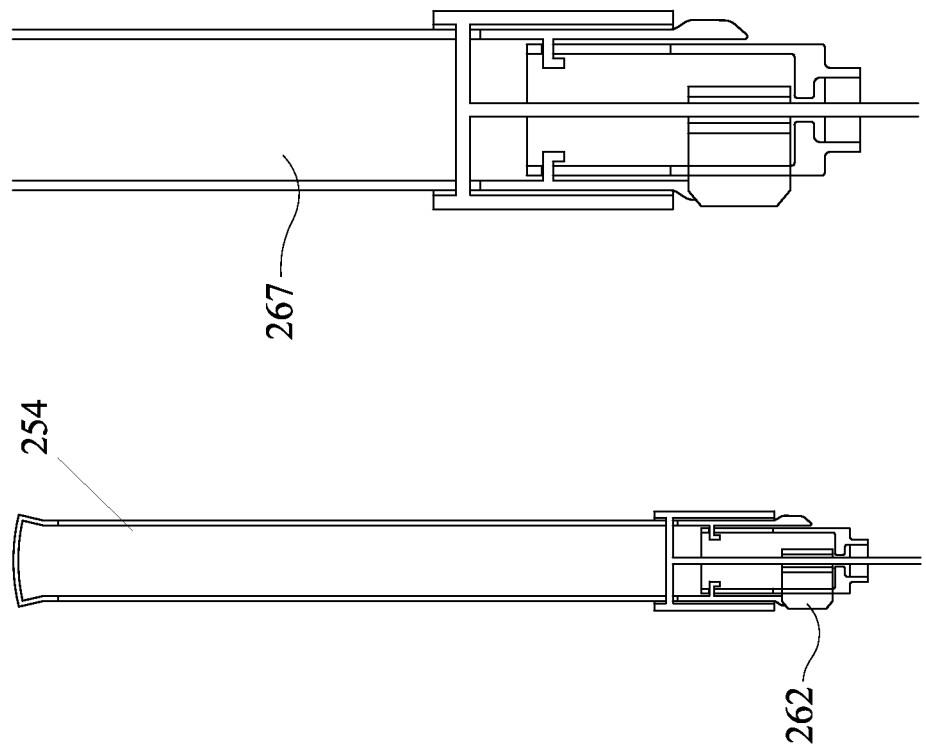
FIG. 27
FIG. 26
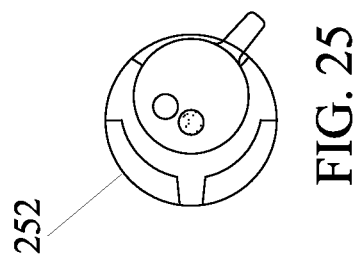
FIG. 25

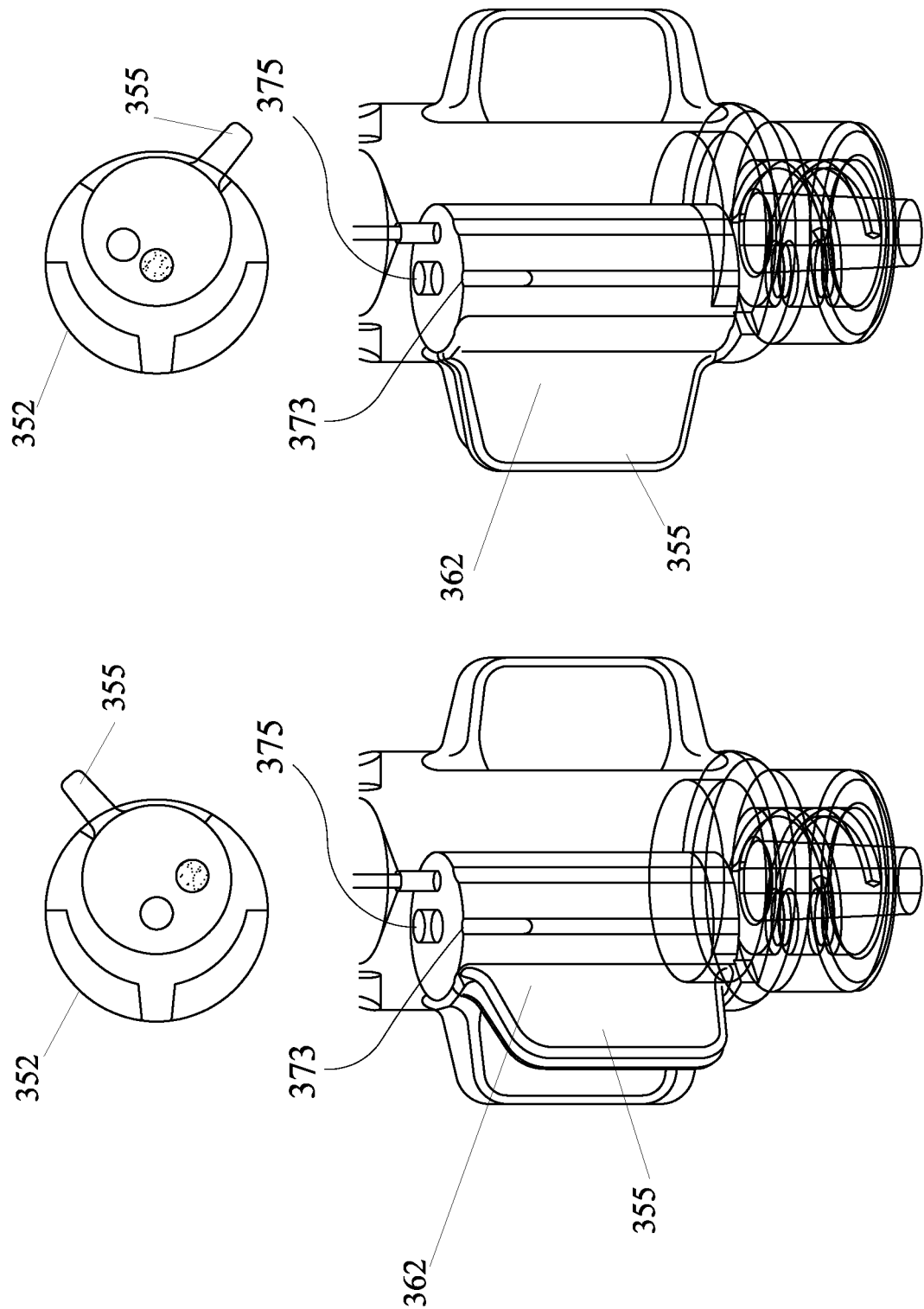

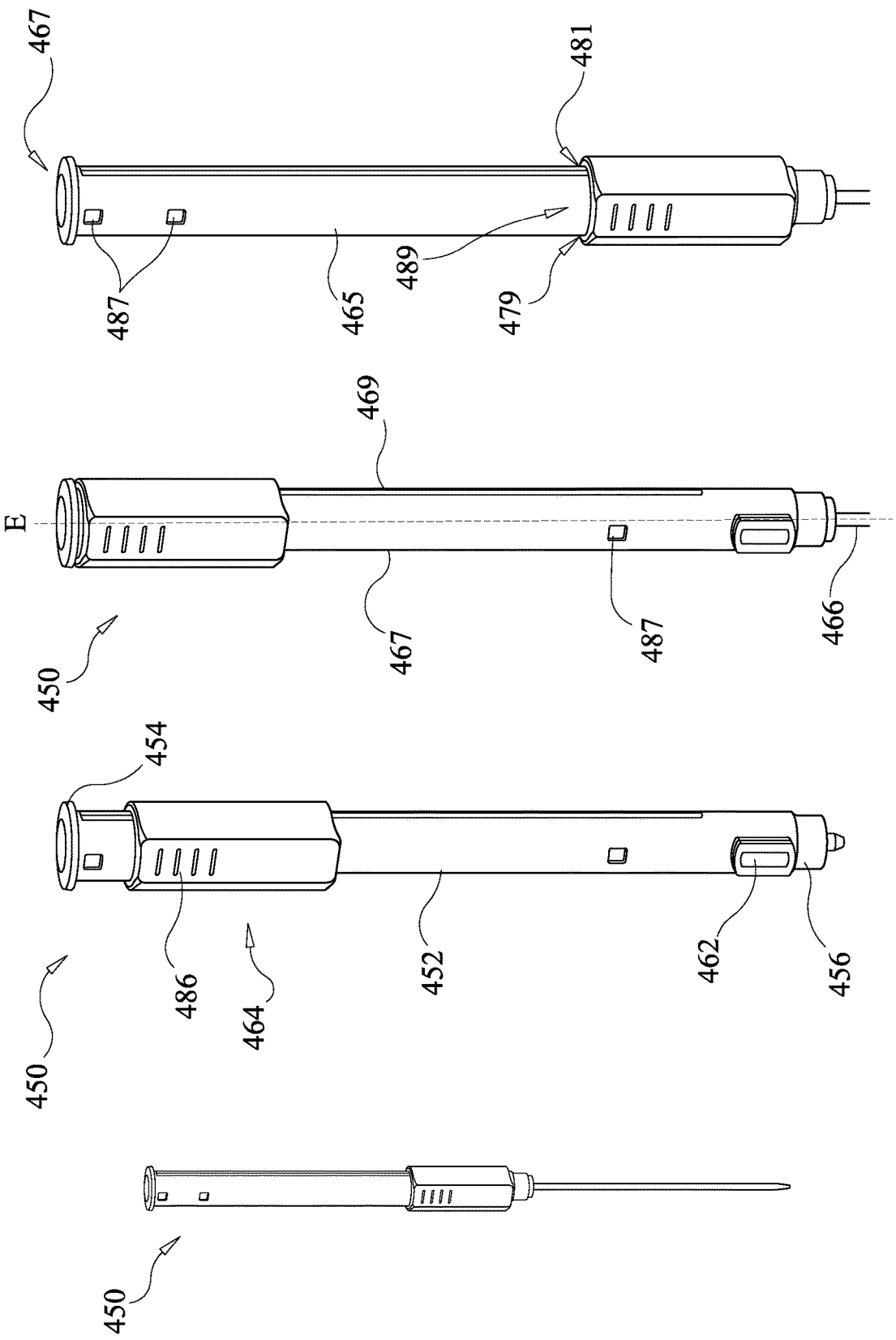

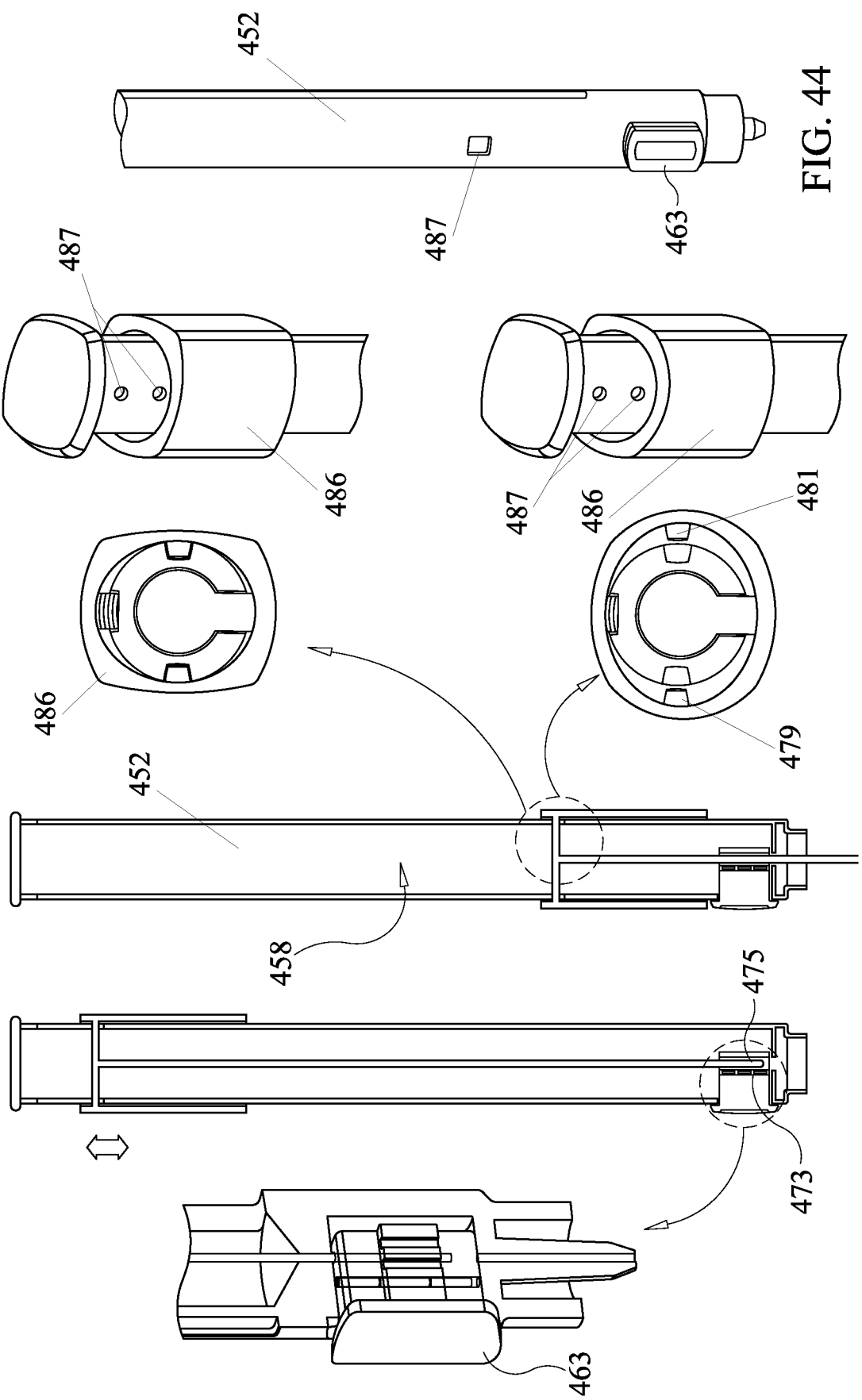

DRUG DELIVERY DEVICE WITH RETAINING MEMBER

CROSS REFERENCE TO RELATED APPLICATIONS

This application is a divisional application of U.S. patent application Ser. No. 14/517,311, filed Oct. 17, 2014, which claims priority from U.S. Provisional Application Ser. No. 61/892,357, filed on Oct. 17, 2013, titled "DRUG DELIVERY DEVICE WITH RETAINING MEMBER" and U.S. Provisional Application Ser. No. 61/892,243, filed on Oct. 17, 2013, titled "DRUG DELIVERY DEVICE WITH RETAINING MEMBER," the entire contents of which are incorporated herein by reference into the present application.

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Previously, drug depots and other types of implants have been inserted into the treatment site beneath the skin by use of a trocar device, which is a two-piece device that includes a cannula and an obdurator. The trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Typically, trocar devices are used to implant drug depots subcutaneously over a large area (e.g., 2-2.5 inches), with a typical drug depot in the order of 1½ inches long. Thus, the trocar device is not suitable for many treatment sites because it lacks precision and may cause additional trauma to the tissue surrounding the site of implant.

Other drug depot devices have been developed to simplify implanting the drug depots. These devices have a handle for one-handed implantation of the drug depot, a needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required. Conventional needle and syringe devices have been used to implant a drug depot to sites such as, for example, the epidural space. These devices typically utilize a syringe preloaded with the drug depot and an epidural needle. The needle is inserted through the skin, supraspinus ligament, intraspinus ligament, ligamentum flavum and then into the epidural space. The drug depot is delivered through the needle to the epidural space using the syringe plunger. Conventional needle and syringe devices often do not easily allow controlled and precision implant of the drug depot. If multiple drug depot implants are needed, these conventional needle and syringe devices often do not allow accurate placement of the implant in a manner so that one drug depot does not substantially interfere with the dissolution of the other.

New drug depot devices are needed, which can easily allow accurate and precise implantation of a drug depot with minimal physical and psychological trauma to a patient. When implanting several drug depots, a drug depot device is needed that accurately and precisely allows placement of the drug depot in a manner such that one depot does not substantially interfere with the dissolution of the others.

SUMMARY

New drug depot devices, which can easily allow accurate and precise implantation of a drug depot with minimal physical and psychological trauma to a patient are provided. One advantage of the drug depot device is that it allows the user to dispense multiple doses of the drug in sequence.

In various embodiments, a drug depot device is provided for delivering a drug to a target tissue site, the drug depot device comprising a body comprising a proximal end and a distal end and a chamber disposed therebetween. An upper portion is disposed about the proximal end of the body. A retaining member is disposed within a wall of the body and is engageable with the chamber, and a plunger is configured for disposal within the upper portion and the chamber. The upper portion is movable about the proximal end of the body to open the chamber such that the plunger is disposed within a passageway defined within the chamber, and movement of the plunger in a distal direction pushes the retaining member such that the drug moves out of the body.

In one embodiment, a drug delivery device is provided for delivering a drug to a target tissue site, the drug delivery device comprising a body comprising a proximal end and a distal end and a chamber comprising a passageway disposed therebetween. An external surface comprises a first guide and a second guide. A retaining member is disposed within a wall defined by the external surface of the body and is engageable with the chamber. An internal plunger comprises a handle and the plunger is configured for disposal within the body. The plunger handle is configured for slidable engagement with the first guide and the second guide and movement of the plunger handle moves the plunger through the passageway of the body and engages with the retaining member such that the drug is dispensed from the delivery device.

In another embodiment, a method of delivering a drug to a target tissue site is provided, the method comprising: introducing a drug delivery device comprising a body comprising a proximal end and a distal end and a chamber comprising a passageway disposed therebetween, an upper portion disposed about the proximal end of the body that rotates about the proximal end of the body to open the chamber, and a retaining member disposed within a wall of the body and engageable with the chamber; attaching a needle with the distal end of the body; inserting a plunger into the passageway, and moving the plunger in a first position to push the retaining member outward and moving the plunger in a second position such that the drug moves through the needle and is ejected from the delivery device and into the target tissue site.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIGS. 7-8 illustrate front views of the embodiment of the drug delivery device as shown in FIGS. 1-3. In some embodiments, the wall of the body comprises an opening configured for visual inspection of the drug.

FIGS. 18-28 illustrate front and side views of an embodiment of the drug delivery device. The drug delivery device comprises a body comprising a proximal end and a distal end and a chamber comprising a passageway disposed therebetween. An external surface comprises a first guide and a second guide. A retaining member is disposed within a wall defined by the external surface of the body and is engageable with the chamber. A needle is configured for engagement with the distal end of the body. Drug delivery device comprises an internal plunger comprising a handle, and is configured for disposal within the body. The plunger handle is configured for slidable engagement with the first guide and the second guide and movement of the plunger handle moves the plunger through the passageway of the body and engages with the retaining member such that the drug moves through the needle and is ejected from the delivery device and into the target tissue site. In some embodiments, the retaining member comprises a first channel and a second channel. In various embodiments, the retaining member is rotatable relative to the body and is transparent and comprises a window configured for visual inspection of the drug. In some embodiments, the body comprises a wing transverse to the distal end of the body. In some embodiments, the retaining member is rotated in a direction such that the plunger is inserted into the first channel during movement of the handle in a distal direction. In various embodiments, the handle is disposed about the external surface of the body and engages the first guide and the second guide via a first inner protuberance and a second inner protuberance.

FIGS. 30-36 illustrate side and detailed views of an embodiment of the drug delivery device. The drug delivery device comprises a body comprising a proximal end and a distal end and a chamber comprising a passageway disposed therebetween. An external surface comprises a first guide and a second guide. A retaining member is disposed within a wall defined by the external surface of the body and is engageable with the chamber. A needle is configured for engagement with the distal end of the body. Drug delivery device comprises an internal plunger comprising a handle, and is configured for disposal within the body. The plunger handle is configured for slidable engagement with the first guide and the second guide and movement of the plunger handle moves the plunger through the passageway of the body and engages with the retaining member such that the drug moves through the needle and is ejected from the delivery device and into the target tissue site. In some embodiments, the retaining member comprises a first channel and a second channel. In various embodiments, the retaining member is rotatable relative to the body and is transparent and comprises a window configured for visual inspection of the drug. In some embodiments, the body comprises a wing transverse to the distal end of the body. In some embodiments, the retaining member is rotated in a direction such that the plunger is inserted into the first channel during movement of the handle in a distal direction. In some embodiments, the handle comprises a first part and a second part and the first part is configured for disposal within the first guide and the second part is configured for disposal within the second guide.

FIGS. 38-44 illustrate an embodiment of the drug delivery device. The drug delivery device comprises a body comprising a proximal end and a distal end and a chamber comprising a passageway disposed therebetween. An external surface comprises a first guide and a second guide. A retaining member is disposed within a wall defined by the external surface of the body and is engageable with the chamber. A needle is configured for engagement with the distal end of the body. Drug delivery device comprises an internal plunger comprising a handle, and is configured for disposal within the body. The plunger handle is configured for slidable engagement with the first guide and the second guide and movement of the plunger handle moves the plunger through the passageway of the body and engages with the retaining member such that the drug moves through the needle and is ejected from the delivery device and into the target tissue site. In some embodiments, the retaining member comprises a first channel and a second channel. In some embodiments, the handle is disposed about the external surface of the body and engages the first guide and the second guide via a first inner protuberance and a second inner protuberance and the handle engages at least a first indent defined by the external surface of the body via a third inner protuberance. In some embodiments, the handle is moved about the body when squeezed. In various embodiments, the retaining member is transparent and comprises a window configured for visual inspection of the drug. In some embodiments, the retaining member is pushed in an inward direction such that the plunger is inserted into the first channel during movement of the handle in a distal direction to deliver the drug to the needle.

Figure 3:
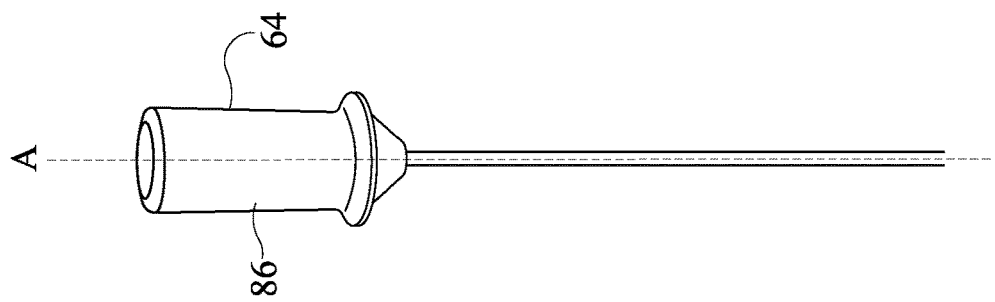
FIGS. 1-3 illustrate front views of one embodiment of a drug delivery device. The drug delivery device comprises a body comprising a proximal end and a distal end and a chamber disposed therebetween; an upper portion disposed about the proximal end of the body; a retaining member disposed within a wall of the body and engageable with the chamber; and a plunger configured for disposal within the upper portion and the chamber. A needle is attached to the distal end of the body. The upper portion is movable about the proximal end of the body to open the chamber such that the plunger is disposed within a passageway defined within the chamber, and movement of the plunger in a distal direction pushes the retaining member outward such that the drug moves through the needle and is ejected from the delivery device and into the target tissue site.
Figure 2:
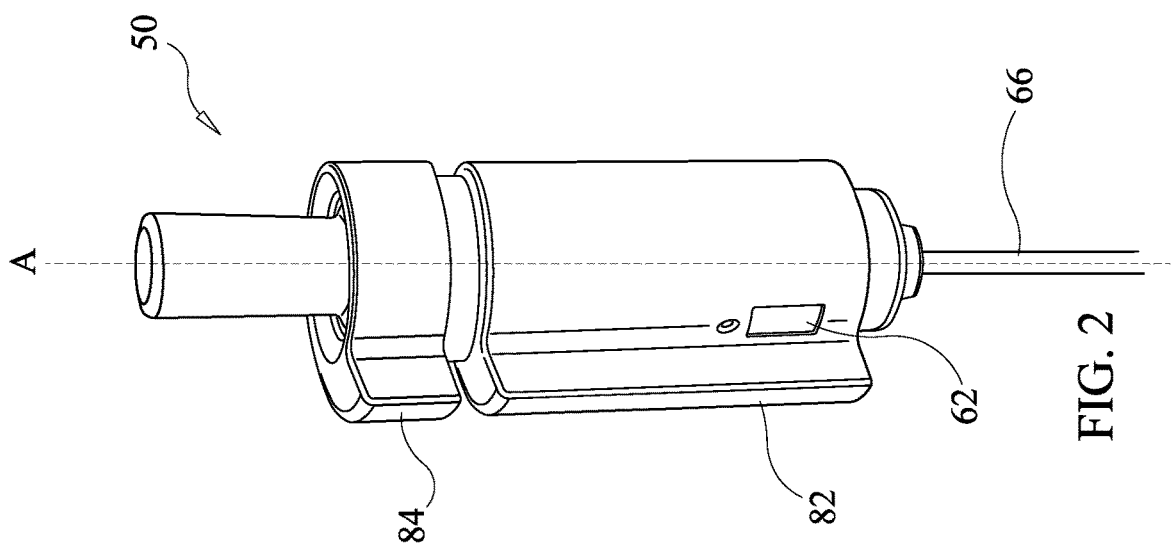
Figure 1:
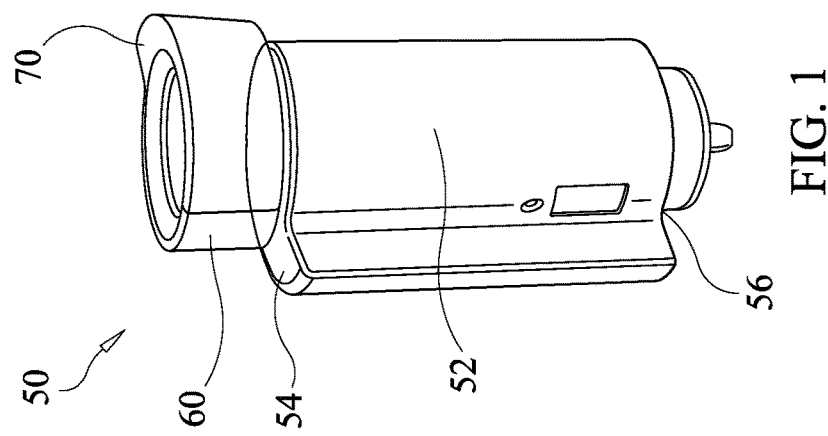
Figure 6:
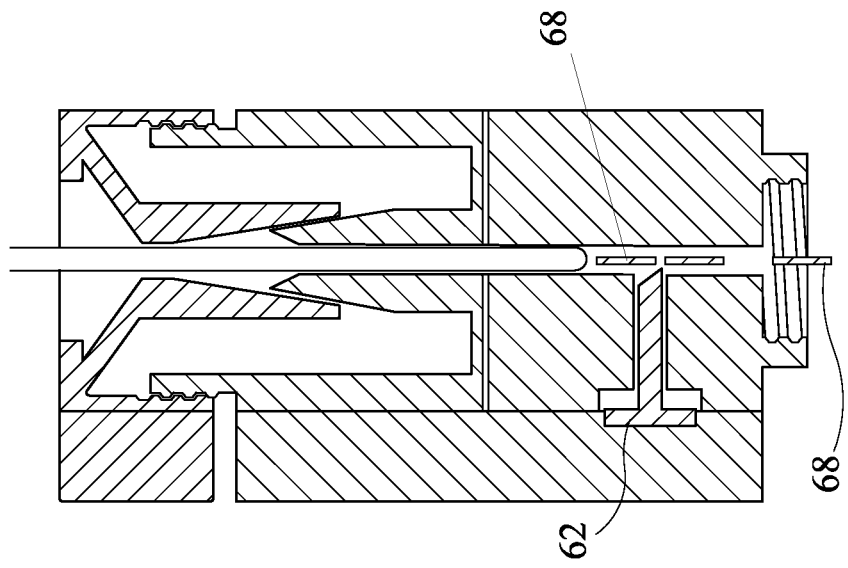
FIGS. 4-6 illustrate cross-sectional views of the embodiment of the drug delivery device shown in FIGS. 1-3. In some embodiments, the upper portion comprises an internally threaded collet and a first tab and a second tab. The collet rotates about a threaded portion at the proximal end of the body and the chamber comprises a third tab and a fourth tab configured for engagement with the first tab and the second tab.
Figure 5:
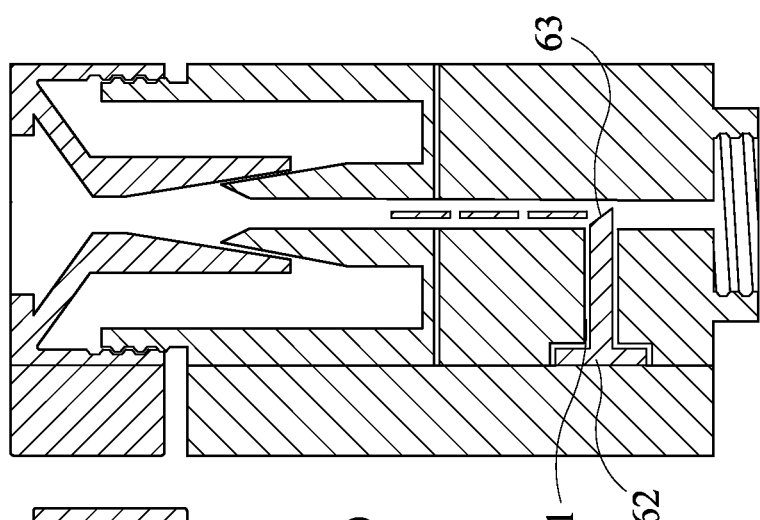
Figure 4:
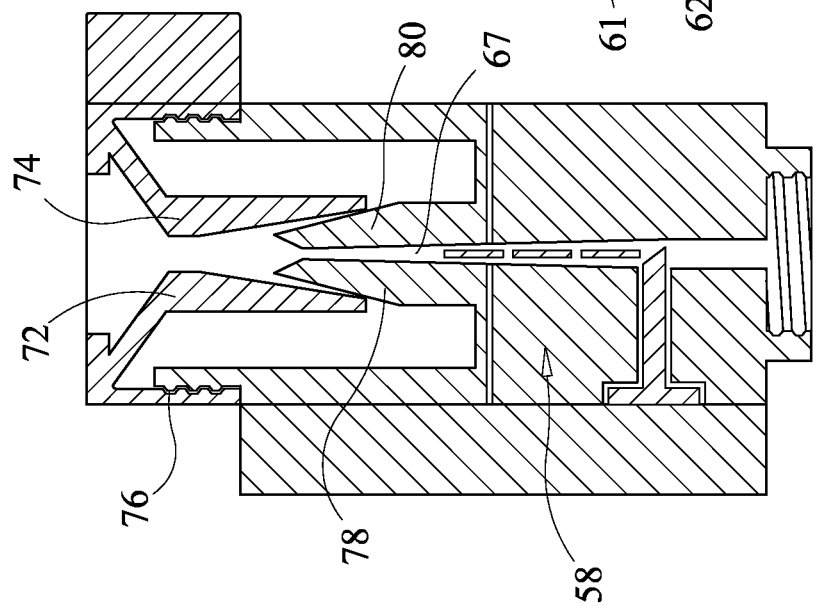

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot devices, which can easily allow the accurate and precise implantation of multiple drug depots with minimal physical and psychological trauma to a patient are provided. In various embodiments the drug depot device allows the user to dispense multiple drug depots, in sequence, to a site beneath the skin of the patient. In various embodiments, when several drug depots are to be implanted, a drug depot device is provided that accurately allows placement of the drug depot in a manner such that one depot does not substantially interfere with the dissolution of the others.

In some embodiments, the drug delivery device contains and protects the drug (e.g., drug pellets) and ensures that the drug cannot be deployed accidentally, minimizing the number of work flow steps for the injection procedure and allowing for visual inspection of the drug.

FIGS. 1-8 illustrate one embodiment of a drug delivery device 50. The drug delivery device comprises a body 52 comprising a proximal end 54 and a distal end 56. Longitudinal axis A extends between the proximal end and the distal end. A chamber 58 is disposed between the proximal end and the distal end. An upper portion 60 is disposed about the proximal end of the body. A retaining member 62 is slidably disposed within a transverse channel 61 defined by a wall of the body, and the retaining member is engageable with the chamber. The retaining member is configured to prevent a drug 68 (e.g., drug depot) from deploying accidentally from the drug delivery device by creating a movable barrier which closes off a passageway 67 defined within the chamber, where the drug may be stored. In some embodiments, the retaining member is variously shaped. In some embodiments, the retaining member is cylindrical, rectangular, pin shaped and/or screw shaped. In various embodiments, the retaining member comprises a distal end 63 configured for engagement with the drug (e.g., drug depot). In some embodiments, the end is variously configured, such as, angled, arcuate, tapered, flat, irregular, and/or grooved. The retaining member is manually pushed inward, thereby moving across the entire horizontal distance of the passageway, closing off the passageway and preventing the drug (e.g., drug depot) from deploying from the drug delivery device. The end of the retaining member will engage with the drug (e.g., drug depot) such that the drug remains above the end of the retaining member. In some embodiments, the retaining member is transverse relative to the body. In some embodiments, the retaining member can be monolithic with the body and is activated when the plunger and/or the drug depot contacts it or it can be a separate piece attached to the body.

A plunger 64 is configured for longitudinal disposal within the upper portion and the chamber. A needle 66 is attached to the distal end of the body. In some embodiments, the needle is detachable from the body of the device. The upper portion is rotatable about the proximal end of the body to open the chamber such that the plunger is disposed within the passageway, and movement of the plunger in a distal direction pushes the retaining member outward such that the drug (e.g., drug depot) moves through the needle and is ejected from the delivery device and into the target tissue site. In various embodiments, the plunger engages the drug and not the needle. In some embodiments, the plunger stops adjacent the needle and the drug ejects from the device via gravity. In some embodiments, the plunger moves through the passageway and passes through the needle to assist in dispensing and ejecting the drug.

In some embodiments, the upper portion comprises an internally threaded collet 70 and comprises a first tab 72 and a second tab 74. The collet rotates about a threaded portion 76 at the proximal end of the body and the chamber comprises a third tab 78 and a fourth tab 80 configured for engagement with the first tab and the second tab. The first and the second tab are configured to guide the drug (e.g., drug depot) through the body using the plunger. In some embodiments, the collet can be attached to the body by other means, such as for example, a rod, pin, screw, clip, etc.

In some embodiments, the body comprises an external first flange 82 and an external second flange 84. In various embodiments, the collet is rotated in a direction, aligning the external first flange and the external second flange together such that the passageway is opened and the plunger is disposed within the passageway. In various embodiments, the first flange indicates alignment of the delivery device with the needle. In some embodiments, rotation of the collet is consistent with rotation to attach the needle to the body. In various embodiments, the plunger comprises a handle 86 configured to snap into the proximal end of the body. In some embodiments, the wall of the body comprises an opening 88 configured for visual inspection of the drug. In some embodiments, the drug depot can be physically inspected by inserting a rod 89 or pin into the opening.

Figure 9:
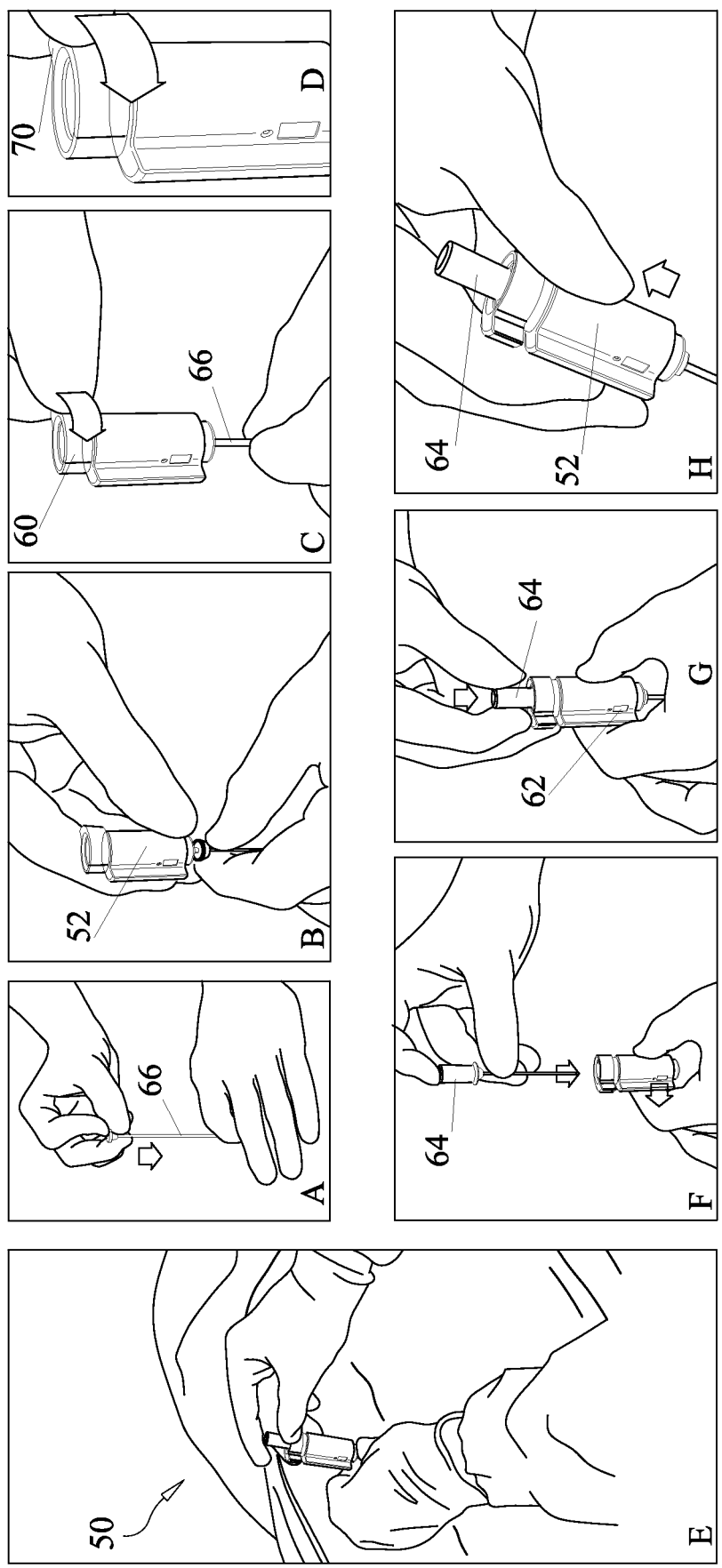
FIG. 9 illustrates a method of delivery of a drug to a target tissue site utilizing the drug delivery device as shown in FIGS. 1-3. A and B illustrate the needle being attached to the body of the device. C and D illustrate the upper portion being rotated. E illustrates the device being positioned over the target tissue site. F and G illustrate the plunger being inserted into the body of the device. The plunger is moved in a downward direction and the drug (e.g., pellets) is then ejected out of the device. H illustrates the entire assembly being removed from the target tissue site.

FIG. 9 illustrates a method of delivery of a drug to a target tissue site utilizing the drug delivery device as shown in FIGS. 1-8. The needle is attached to the body of the device and the upper portion is rotated. The plunger is inserted into the body of the device. The plunger is moved in a downward direction into and through the passageway. As the plunger moves, it contacts the retaining member, moving the retaining member in an outward direction to open the passageway. The plunger contacts the drug (e.g., pellets), and the drug is ejected out of the device. The entire assembly is then removed from the target tissue site.

Figure 12:
FIGS. 10-12 illustrate front views of an embodiment of the drug delivery device. The drug delivery device comprises a body comprising a proximal end and a distal end and a chamber is disposed therebetween comprising a passageway. A retaining member is disposed within a wall of the body and is engageable with the chamber. A needle is attached to the distal end of the body. The device comprises a plunger that is configured for insertion at the proximal end of the device and is configured for disposal within the body of the device. Movement of the plunger in a distal direction pushes the retaining member outward such that the drug moves through the needle and is ejected from the delivery device and into the target tissue site.
Figure 11:
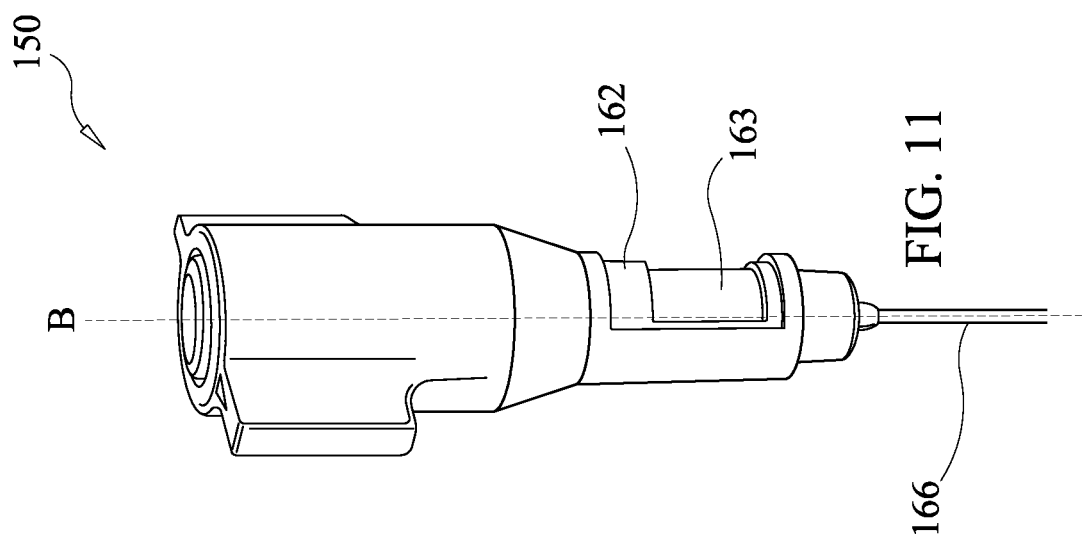
Figure 10:
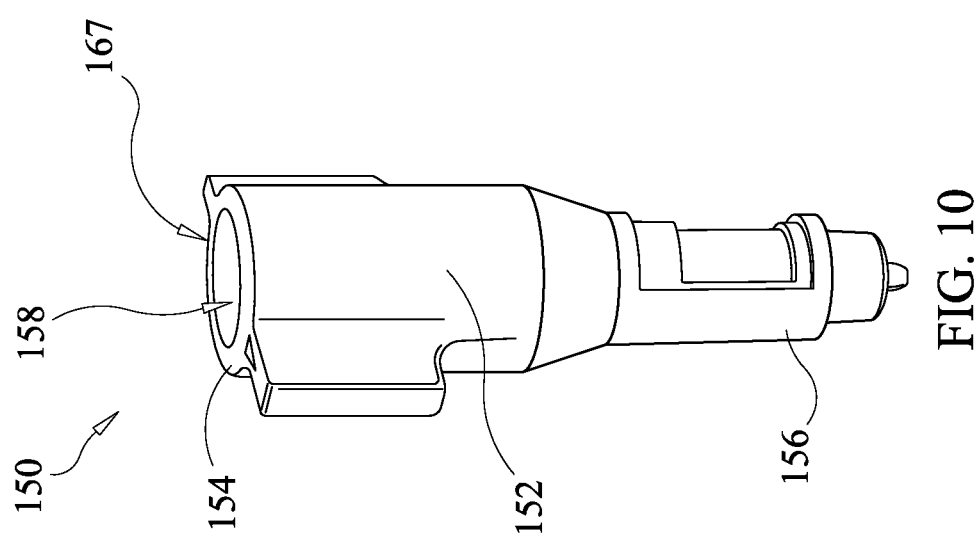
Figure 15:
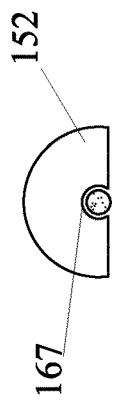
FIGS. 13-16 illustrate front and side views respectively of the embodiment of the drug delivery device as shown in FIGS. 10-12. In some embodiments, the retaining member is transparent and comprises a window configured for visual inspection of the drug. In some embodiments, the retaining member engages with the wall of the body via snap fit engagement with press fit posts, adhesive, solvent welded, heat welded, spring loaded or magnetic engagement.
Figure 16:
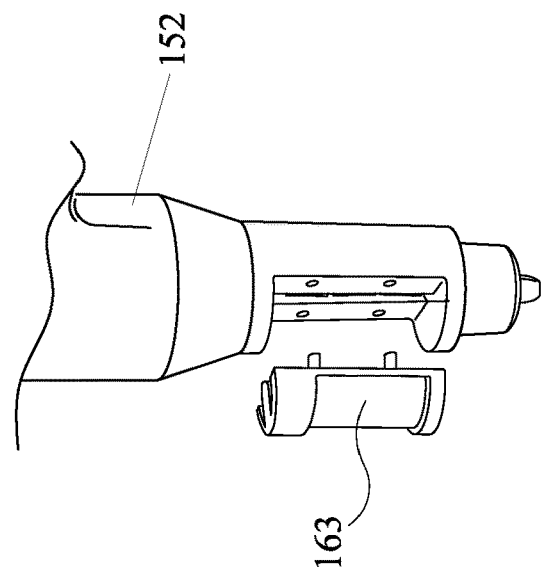
Figure 14:
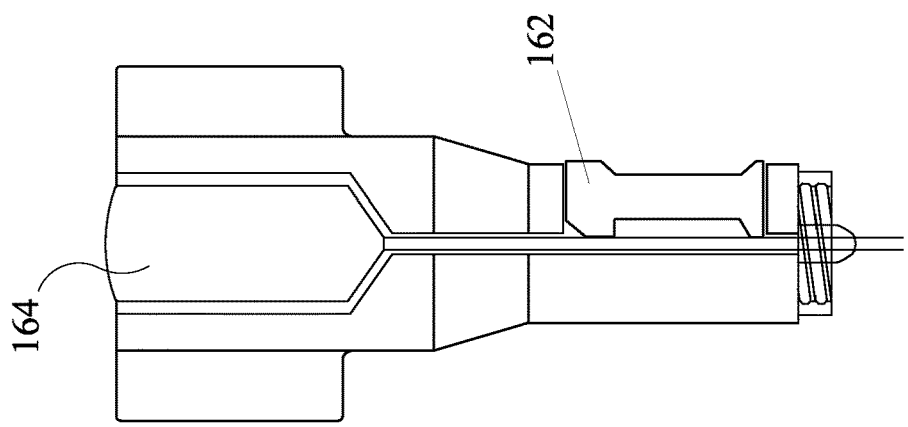
Figure 13:
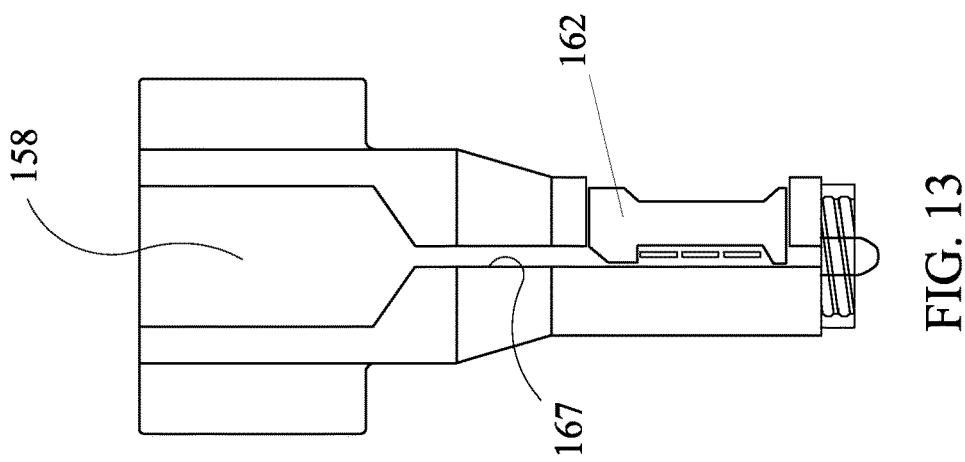

FIGS. 10-12 illustrate one embodiment of the drug delivery device 150. The drug delivery device comprises a body 152 comprising a proximal end 154 and a distal end 156 and a chamber 158 disposed therebetween comprising a passageway 167. A longitudinal axis B extends between the proximal end and the distal end. A retaining member 162 is disposed within a wall of the body and engageable with the chamber. The retaining member is configured to prevent the drug (e.g., drug depot) from deploying accidentally from the drug delivery device by creating a movable barrier which closes off the passageway, where the drug may be stored. The device comprises a plunger 164 that is configured for longitudinal insertion at the proximal end of the device and is configured for disposal within the body of the device. A needle 166 is attached to the distal end of the body. Movement of the plunger in a distal direction pushes the retaining member outward such that the drug moves through the needle and is ejected from the delivery device and into the target tissue site. In various embodiments, the plunger engages the drug and not the needle. In some embodiments, the plunger stops adjacent the needle and the drug ejects from the device via gravity. In some embodiments, the plunger moves through the passageway and passes through the needle to assist in dispensing and ejecting the drug.

In some embodiments, the retaining member is transparent and comprises a window 163 configured for visual inspection of the drug. In some embodiments, the retaining member engages with the wall of the body via snap fit engagement with press fit posts, adhesive, solvent welded, heat welded, spring loaded or magnetic engagement. In various embodiments, the retaining member is variously shaped. In some embodiments, the retaining member is cylindrical, rectangular, pin shaped and/or screw shaped. In some embodiments, the retaining member is transverse relative to the body.

Figure 17:
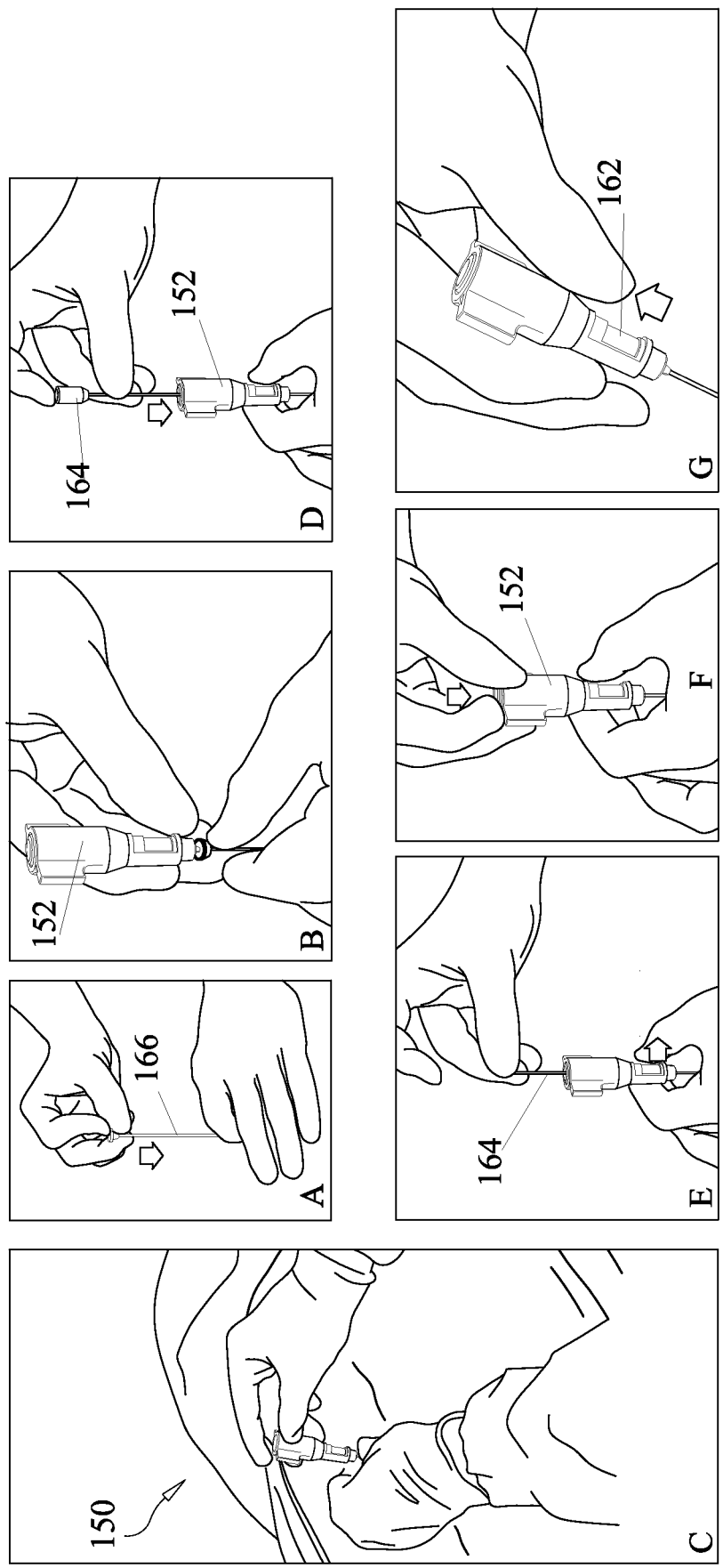
FIG. 17 illustrates a method of delivery of a drug to a target tissue site utilizing the drug delivery device as shown in FIGS. 10-12. A and B illustrate the needle being attached to the body of the device. C illustrates the device being positioned over the target tissue site. D-F illustrates the plunger being inserted into the body of the device. The plunger is moved in a downward direction and the drug (e.g., pellets) is then ejected out of the device. The entire assembly fits completely into the body of the drug delivery device. G illustrates the entire assembly being removed from the target tissue site.
Figure 24:
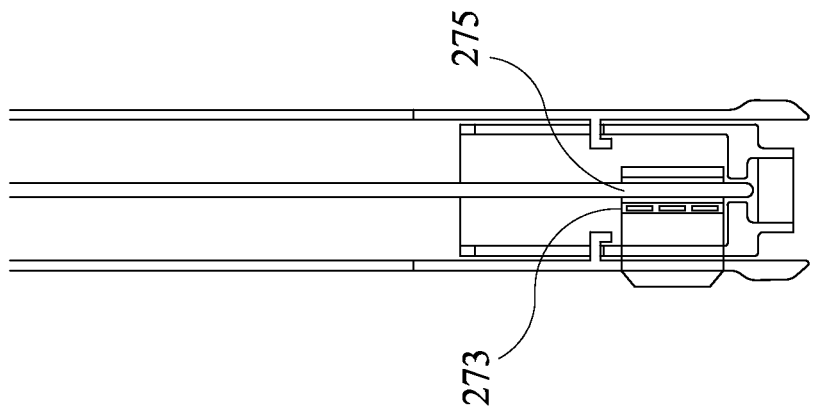
Figure 23:
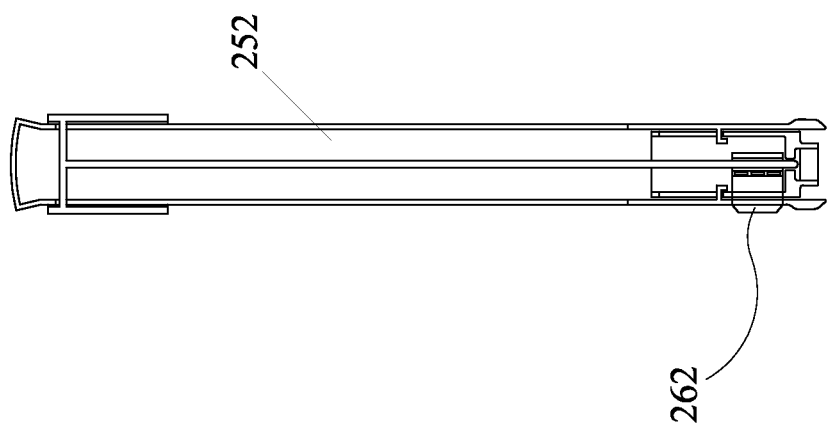
Figure 22:
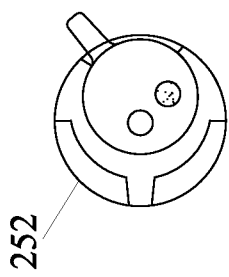

FIG. 17 illustrates a method of delivery of a drug to a target tissue site utilizing the drug delivery device as shown in FIGS. 10-12. A needle is attached to the body of the drug delivery device. A plunger is inserted into the body of the drug delivery device. The plunger is moved in a downward direction into and through the passageway. As the plunger moves, it contacts the retaining member, moving the retaining member in an outward direction to open the passageway. The plunger contacts the drug (e.g., pellets), and the drug is ejected out of the device. The entire assembly fits completely into the body of the drug delivery device. The drug delivery device is then removed from the target tissue site.

FIGS. 18-28 illustrate an embodiment of the drug delivery device 250. The drug delivery device comprises a body 252 comprising a proximal end 254 and a distal end 256 and a chamber 258 comprising a passageway 267 disposed therebetween. A longitudinal axis C extends between the proximal end and the distal end. An external surface 265 comprises a first guide 269 and a second guide 271. A retaining member 262 is disposed within a wall defined by the external surface of the body and is engageable with the chamber. The retaining member is configured to prevent the drug (e.g., drug depot) from deploying accidentally from the drug delivery device. In various embodiments, the retaining member is variously shaped. In some embodiments, the retaining member is cylindrical, rectangular, pin shaped and/or screw shaped. In some embodiments, the retaining member comprises an external tab 255 configured to facilitate rotatable movement of the retaining member. In some embodiments, the retaining member is transverse relative to the body.

A needle 266 is configured for engagement with the distal end of the body. Drug delivery device comprises an internal plunger 264 comprising a handle 286, and is configured for longitudinal disposal within the body. The plunger handle is configured for slidable engagement with the first guide and the second guide and movement of the plunger handle moves the plunger through the passageway of the body and engages with the retaining member such that the drug moves through the needle and is ejected from the delivery device and into the target tissue site. In various embodiments, the plunger engages the drug and not the needle. In some embodiments, the plunger stops adjacent the needle and the drug ejects from the device via gravity. In some embodiments, the plunger moves through the passageway and passes through the needle to assist in dispensing and ejecting the drug.

In some embodiments, the retaining member comprises a first channel 273 and a second channel 275. At least one of the channels is configured for disposal of the drug (e.g., drug depot). In various embodiments, the retaining member is rotatable relative to the body and is transparent and comprises a window 263 configured for visual inspection of the drug. In various embodiments, the body comprises a wing 277 transverse to the distal end of the body. In some embodiments, the wing is a grip portion which assists in the handling of the drug delivery device during use. In some embodiments, the retaining member is rotated in a direction such that the plunger is inserted into the first channel during movement of the handle in a distal direction. In various embodiments, the handle is disposed about the external surface of the body and engages the first guide and the second guide via a first inner protuberance 279 and a second inner protuberance 281.

Figure 29:
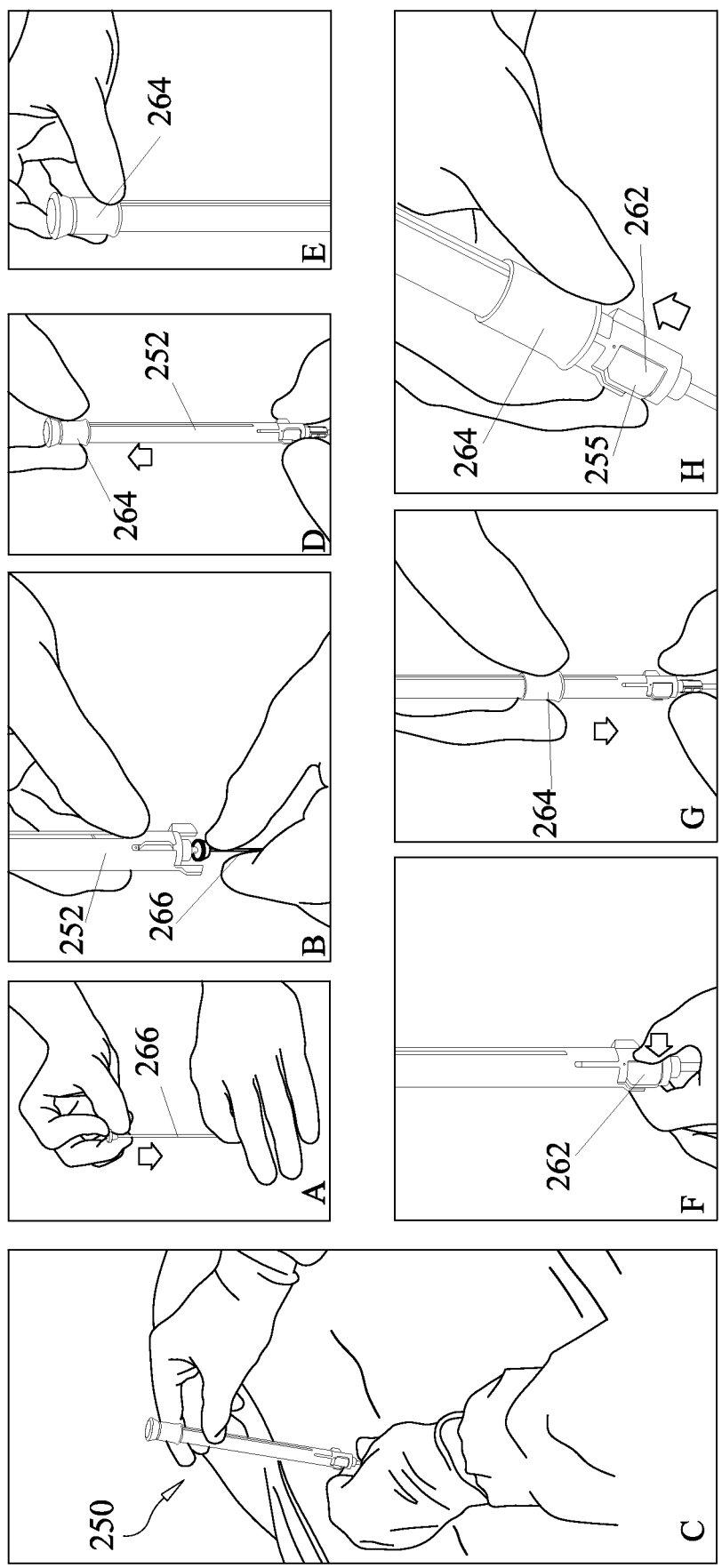
FIG. 29 illustrates a method of delivery of a drug to a target tissue site utilizing the drug delivery device as shown in FIGS. 18-28. A and B illustrate the needle being attached to the body of the device. C illustrates the device being positioned over the target tissue site. D and E illustrate the plunger being retracted to the proximal end of the device. F illustrates that the retaining member is then rotated into place. G illustrates the handle of the plunger being gripped and moved in a downward direction, and the drug (e.g., pellets) is then ejected out of the device. H illustrates the drug delivery device being removed from the target tissue site.
Figure 32:
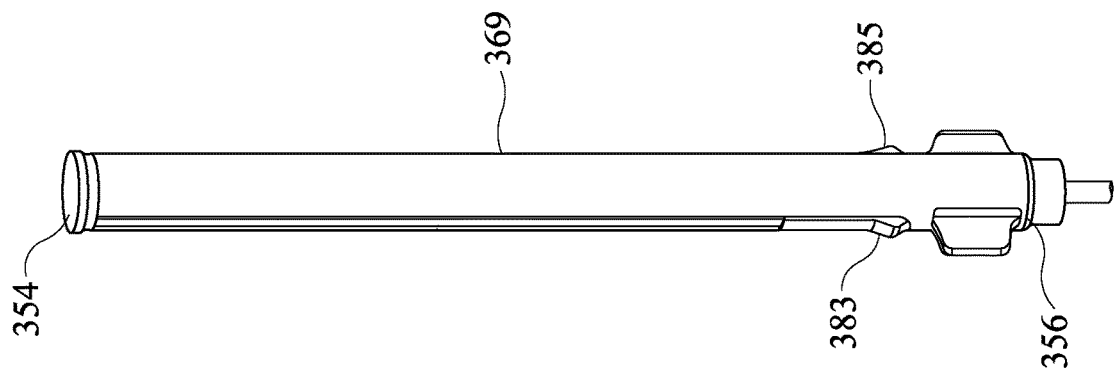
Figure 31:
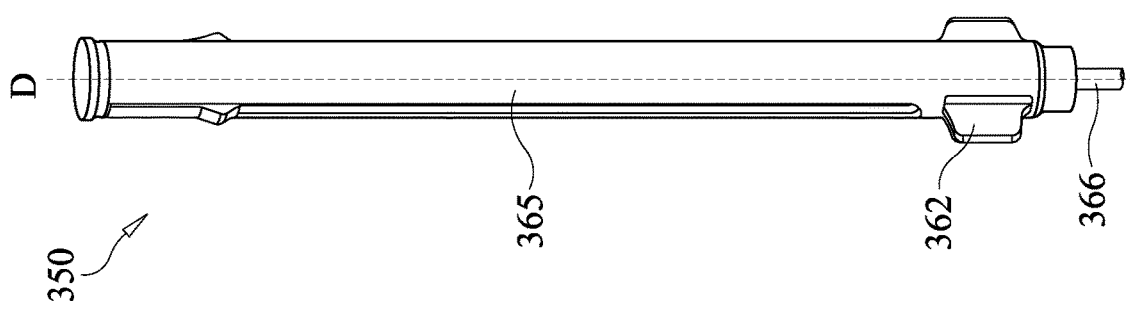
Figure 30:
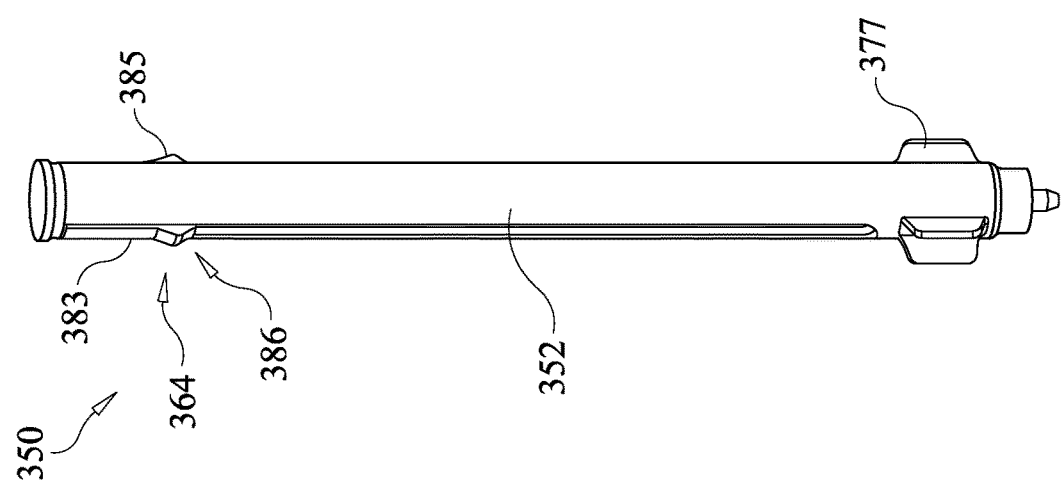
Figure 36:
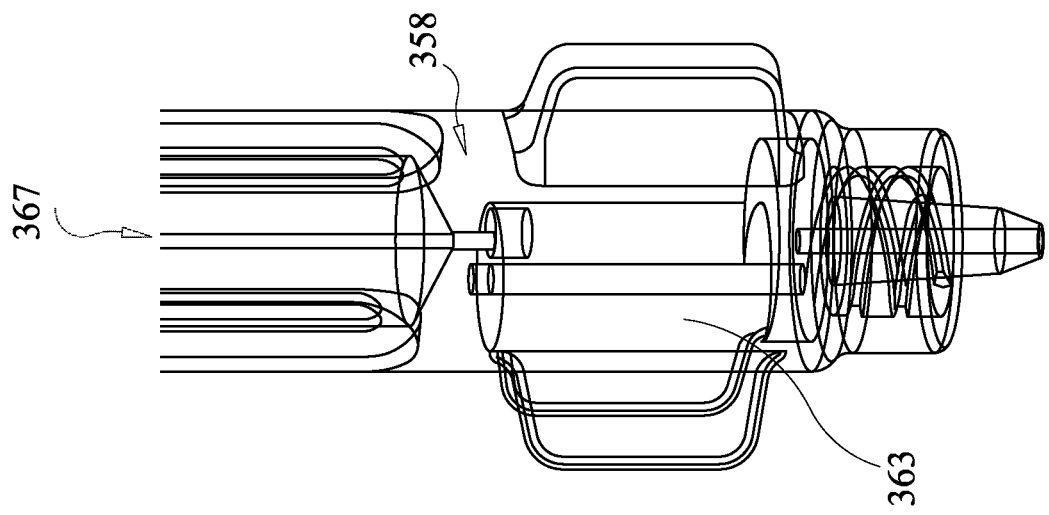
Figure 35:
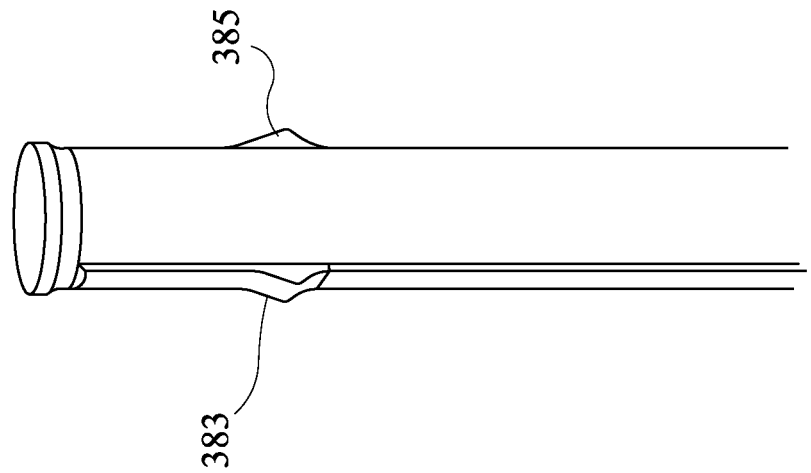

FIG. 29 illustrates a method of delivery of a drug to a target tissue site utilizing the drug delivery device as shown in FIGS. 18-28. A needle is attached to the body of the drug delivery device. The plunger is retracted to the proximal end of the device. The retaining member is then rotated into place. The handle of the plunger is then gripped and moved in a downward direction, moving the plunger into and through the passageway, and into the channel where the drug (e.g., pellets) is disposed. The drug is pushed and ejected out of the device via downward movement of the plunger through the channel. The drug delivery device is then removed from the target tissue site.

FIGS. 30-36 illustrate an embodiment of the drug delivery device 350. The drug delivery device comprises a body 352 comprising a proximal end 354 and a distal end 356 and a chamber 358 comprising a passageway 367 disposed therebetween. A longitudinal axis D extends between the proximal end and the distal end. An external surface 365 comprises a first guide 367 and a second guide 369. A retaining member 362 is disposed within a wall defined by the external surface of the body and is engageable with the chamber. The retaining member is configured to prevent the drug (e.g., drug depot) from deploying accidentally from the drug delivery device. In various embodiments, the retaining member is variously shaped. In some embodiments, the retaining member is cylindrical, rectangular, pin shaped and/or screw shaped. In some embodiments, the retaining member comprises an external tab 355 configured to facilitate rotatable movement of the retaining member. In some embodiments, the retaining member is transverse relative to the body.

A needle 366 is configured for engagement with the distal end of the body. Drug delivery device comprises an integrated internal plunger 364 comprising a handle 386, and is configured for longitudinal disposal within the body. The plunger handle is configured for slidable engagement with the first guide and the second guide and movement of the plunger handle moves the plunger through the passageway of the body and engages with the retaining member such that the drug moves through the needle and is ejected from the delivery device and into the target tissue site. In various embodiments, the plunger engages the drug and not the needle. In some embodiments, the plunger stops adjacent the needle and the drug ejects from the device via gravity. In some embodiments, the plunger moves through the passageway and passes through the needle to assist in dispensing and ejecting the drug.

In some embodiments, the retaining member comprises a first channel 373 and a second channel 375. At least one of the channels is configured for disposal of the drug (e.g., pellets). In various embodiments, the retaining member is rotatable relative to the body and is transparent and comprises a window 363 configured for visual inspection of the drug. In various embodiments, the body comprises a wing 377 transverse to the distal end of the body. In some embodiments, the wing is a grip portion which assists in the handling of the drug delivery device during use. In some embodiments, the retaining member is rotated in a direction such that the plunger is inserted into the first channel during movement of the handle in a distal direction. In some embodiments, the handle comprises a first part 383 and a second part 385 and the first part is configured for disposal within the first guide and the second part is configured for disposal within the second guide.

Figure 37:
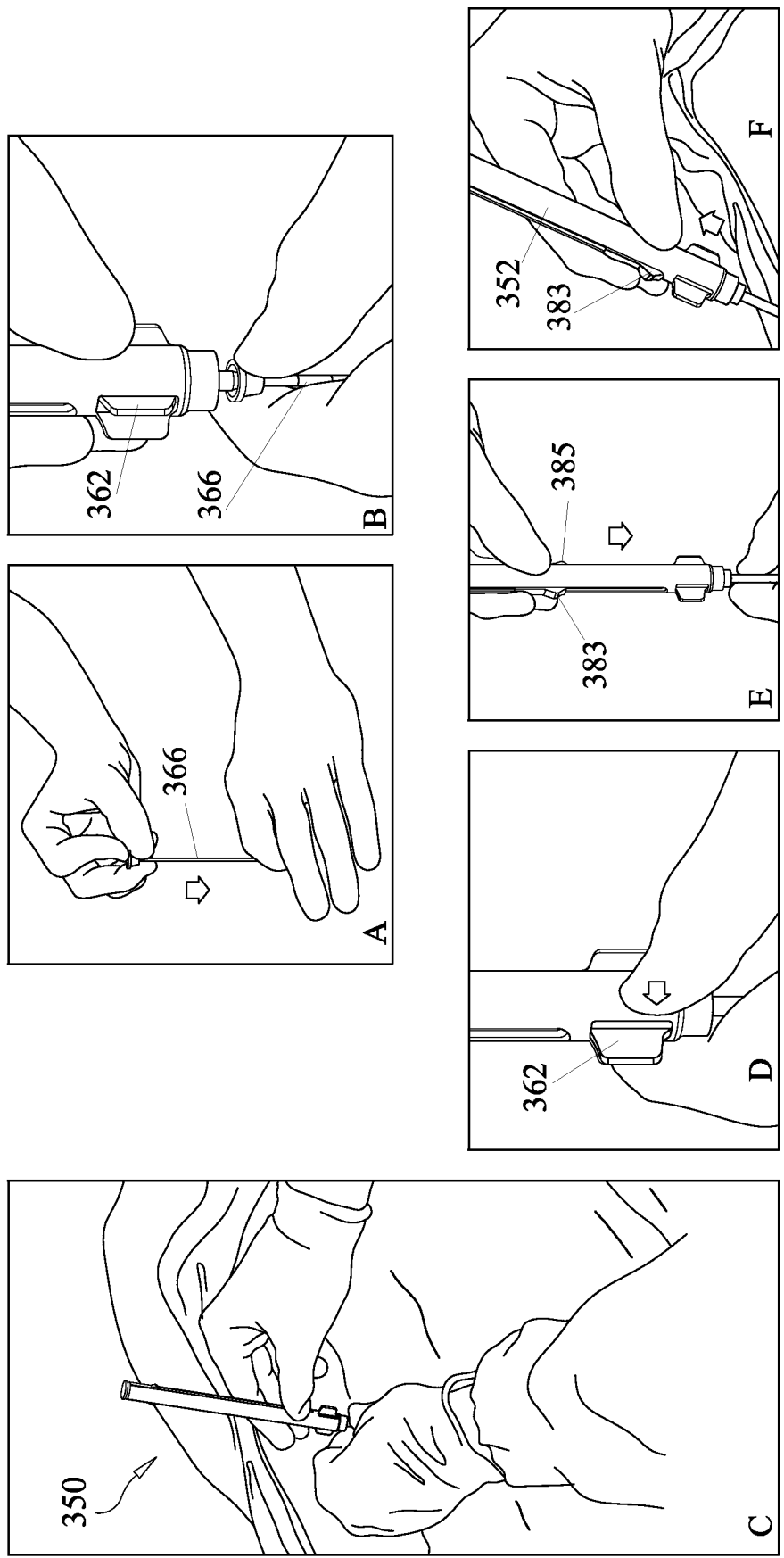
FIG. 37 illustrates a method of delivery of a drug to a target tissue site utilizing the drug delivery device as shown in FIGS. 30-36. A and B illustrate a needle being attached to the body of the device. C illustrates the device being positioned over the target tissue site. The plunger is retracted to the proximal end of the device. D illustrates the retaining member being rotated into place. E illustrates the handle of the plunger being gripped and moved in a downward direction, and the drug (e.g., pellets) is then ejected out of the device. F illustrates the drug delivery device being removed from the target tissue site.

FIG. 37 illustrates a method of delivery of a drug to a target tissue site utilizing the drug delivery device as shown in FIGS. 30-36. A needle is attached to the body of the drug delivery device. The plunger is retracted to the proximal end of the device. The retaining member is then rotated into place via the tab. The handle of the plunger is then gripped and moved in a downward direction into and through the passageway, and into the channel where the drug (e.g., pellets) is disposed. The drug is pushed and ejected out of the device via downward movement of the plunger through the channel. The drug delivery device is then removed from the target tissue site.

FIGS. 38-44 illustrate an embodiment of the drug delivery device 450. The drug delivery device comprises a body 452 comprising a proximal end 454 and a distal end 456 and a chamber 458 comprising a passageway 467 disposed therebetween. A longitudinal axis E extends between the proximal end and the distal end. An external surface 465 comprises a first guide 467 and a second guide 469. A retaining member 462 is disposed within a wall defined by the external surface of the body and is engageable with the chamber. The retaining member is configured to prevent the drug (e.g., drug depot) from deploying accidentally from the drug delivery device. In various embodiments, the retaining member is variously shaped. In some embodiments, the retaining member is cylindrical, rectangular, pin shaped and/or screw shaped. In some embodiments, the retaining member is transverse relative to the body.

A needle 466 is configured for engagement with the distal end of the body. Drug delivery device comprises an integrated internal plunger 464 comprising a handle 486, and configured for longitudinal disposal within the body. The plunger handle is configured for slidable engagement with the first guide and the second guide and movement of the plunger handle moves the plunger through the passageway of the body and engages with the retaining member such that the drug moves through the needle and is ejected from the delivery device and into the target tissue site. In various embodiments, the plunger engages the drug and not the needle. In some embodiments, the plunger stops adjacent the needle and the drug ejects from the device via gravity. In some embodiments, the plunger moves through the passageway and passes through the needle to assist in dispensing and ejecting the drug.

In some embodiments, the retaining member comprises a first channel 473 and a second channel 475. At least one of the channels is configured for disposal of the drug (e.g., pellets). In some embodiments, the handle is disposed about the external surface of the body and engages the first guide and the second guide via a first inner protuberance 479 and a second inner protuberance 481 and the handle engages at least a first indent 487 defined by the external surface of the body via a third inner 489 protuberance. In some embodiments, the handle is moved about the body when squeezed. In various embodiments, the retaining member is transparent and comprises a window 463 configured for visual inspection of the drug. In some embodiments, the retaining member is pushed in an inward direction such that the plunger is inserted into the first channel during movement of the handle in a distal direction to deliver the drug to the needle.

Figure 45:
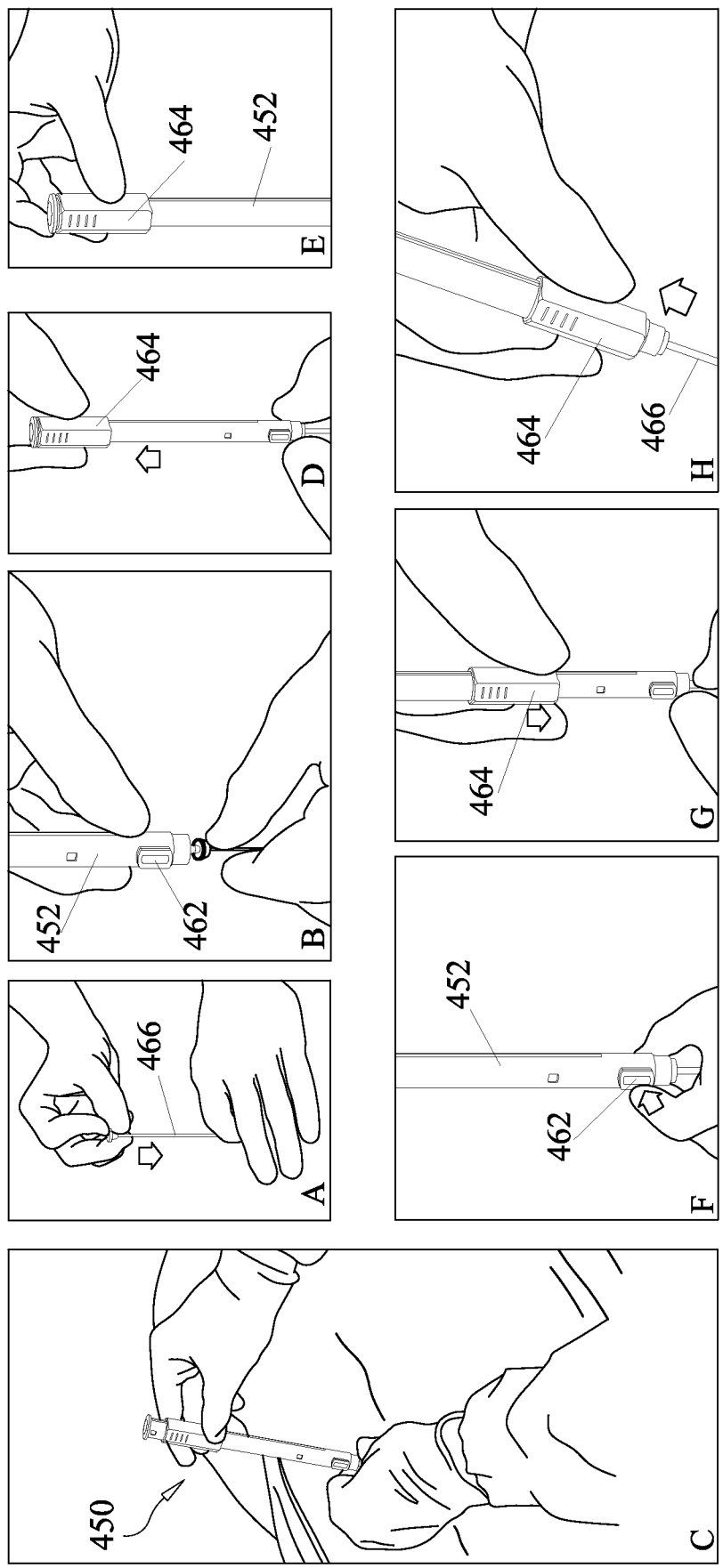
FIG. 45 illustrates a method of delivery of a drug to a target tissue site utilizing the drug delivery device as shown in FIGS. 38-44. A and B illustrate a needle being attached to the body of the device. C illustrates the device being positioned over the target tissue site. D and E illustrate the plunger handle being squeezed and retracted to the proximal end of the device. F illustrates the retaining member being pushed in an inward direction and being flush with the body. G illustrates the handle of the plunger being slided and moved in a downward direction, and the drug (e.g., pellets) is then ejected out of the device. H illustrates the drug delivery device being removed from the target tissue site.

FIG. 45 illustrates a method of delivery of a drug to a target tissue site utilizing the drug delivery device as shown in FIGS. 38-44. A needle is attached to the body of the drug delivery device. The plunger handle is squeezed and retracted to the proximal end of the device. The retaining member is then pushed in an inward direction and is flush with the body. The handle of the plunger is then slided and moved in a downward direction into and through the passageway, and into the channel where the drug (e.g., pellets) is disposed. The drug is pushed and ejected out of the device via downward movement of the plunger through the channel. The drug delivery device is then removed from the target tissue site.

Cannula or Needle

The cannula or needle of the drug depot device is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, nitinol, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. In some embodiments, the length of the cannula is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 1120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 mm. The thickness of the cannula or needle will also depend on the site of implantation. In various embodiments, the thickness includes, but is not limited to, from about 0.05 to about 1.655 mm. In some embodiments, the thickness of the cannula or needle is about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65 or 1.655 mm. The gauge of the cannula or needle may be the widest or smallest diameter or a diameter in between for insertion into a human or animal body. The widest diameter is typically about 14 gauge, while the smallest diameter is about 25 gauge. In various embodiments, the gauge of the needle or cannula is about 17 to about 25 gauge. In some embodiments, the gauge of the needle or cannula is about 17, 18, 19, 20, 21, 22, 23, 24 or about 25 gauge.

In various embodiments, the plunger, cannula or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, the drug depot comprises a drug cartridge containing drug pellets loaded within the chamber of the drug cartridge, when the plunger is moved to the extended position, the drug cartridge will remain within the housing and the chamber of the drug cartridge will guide the tip of the plunger longitudinally and the drug pellet will be released from it when it is in the extended position. A subsequent or second pellet may be administered by repositioning the needle at a target site, removing the plunger so that it is at a position above the drug cartridge, and rotating the drug cartridge at a position horizontal to the plunger and cannula to align the drug chamber and drug depot with the cannula and plunger. The plunger is then slid in a vertical direction within the housing to release the drug depot from the chamber into the cannula where the drug depot can be delivered to the target site by pushing it out the tip of the needle using the plunger. In this way, sequential delivery of a drug can be accomplished. Thus, the above procedure (e.g., repositioning the needle, removing the plunger, rotating the drug cartridge, inserting the plunger, delivering the drug depot) can be repeated multiple times to deliver multiple drug depots to the target tissue site.

In various embodiments, surrounding the opening of the proximal end of the cannula or needle is a generally cylindrical hub having an engagement means (shown as internal threading) for engaging the housing. Engagement means include, but are not limited to, threading, tracks, clips, ribs, projections, and the like that allow a secure connection between the housing and the proximal end of the cannula. For example, in various embodiments the engagement means may be a luer lock connection, where the cannula has mating threads that mate with the threads disposed on or in the housing.

Body

The body may be of various shapes including, but not limited to, cylindrical or round such that the body allows for the affixation to the cannula as well as the drug cartridge and the plunger.

The body may comprise a variety of materials, such as, for example, polyurethane, polyurea, polyether(amide), PEBA, thermoplastic elastomeric olefin, copolyester, and styrenic thermoplastic elastomer, steel, nitinol, aluminum, stainless steel, titanium, metal alloys with high non-ferrous metal content and a low relative proportion of iron, carbon fiber, glass fiber, plastics, ceramics or combinations thereof.

Like the cannula or needle, in various embodiments, the body may have dose indicator markings (e.g., numbers, lines, letters, radiographic markers, etc.) to indicate the number of drug depots delivered. In various embodiments, the plunger includes markings that indicate location at or near the site beneath the skin.

The body may have contours and allow easy grasping of the device during use for insertion of the drug depot. The body can be angled for right and left hand users or can be generic for both hands. In various embodiments, the body can comprise an upper opening, a middle opening, and a lower opening. The upper, middle and lower openings allow a plunger to slide through the openings.

Plunger

Although the first end of the plunger is shown as a knob, it will be understood that the knob can be a top, dial, cap, handle or any member that allows the user to utilize the plunger. The plunger has a second end that includes a tip, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site. In some embodiments, the plunger is external or outside of the body. In some embodiments, the plunger is an integrated internal plunger longitudinally disposed within the body.

The plunger has a diameter less than the cannula or needle so that it can be slidably received therein. The plunger may be longer, the same size, or smaller in length than the cannula or needle. In embodiments where the plunger extends from the distal end of the cannula or needle, the plunger is usually longer than the cannula or needle. In some embodiments, the tip of the plunger can be sharp or blunt. The sharper tip of the plunger can be used in embodiments where the drug cartridge has superior and inferior covers that the sharp tip of the plunger can pierce.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug pellet, allows the plunger tip to snuggly fit within the end of the drug pellet for easier drug delivery. The drug pellet may have a rounded end for easier insertion at the desired site.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[4-[C2-pyridinylamino) sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide polyglycolide (PGA), D-lactide, D,L-lactide, L-lactide, D,L-lactide-ε-caprolactone, D,L-lactide-glycolide-ε-caprolactone or a combination thereof.

In various embodiments, the drug depot comprises drug pellets loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, the drug depot is in the form of a pellet. The pellet can be any shape, such as for example, bullet shaped, spherical, substantially spherical, flaked, rod shaped, square, oval, etc. In various embodiments, an aspect ratio (a ratio of the length of the pellet divided by the width found at an angle of 90° in respect to the length) which is less than about 1.4 to about 1.05. The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc.

In various embodiments, the non-biodegradable material can have a molecular weight of about 2,000 Daltons (Da) to about 3,000,000 Da. In some embodiments, the suitable materials have a molecular weight of about 2,000, 5,000, 10,000, 15,000, 20,000, 25,000, 30,000, 35,000, 40,000, 45,000, 50,000, 55,000, 60,000, 65,000, 70,000, 75,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,025,000, 1,050,000, 1,100,000, 1,150,000, 1,200,000, 1,250,000, 1,300,000, 1,350,000, 1,400,000, 1,450,000, 1,500,000, 1,550,000, 1,600,000, 1,650,000, 1,700,000, 1,750,000, 1,800,000, 1,850,000, 1,900,000, 1,950,000, 2,000,000, 2,025,000, 2,050,000, 2,100,000, 2,150,000, 2,200,000, 2,250,000, 2,300,000, 2,350,000, 2,400,000, 2,450,000, 2,500,000, 2,550,000, 2,600,000, 2,650,000, 2,700,000, 2,750,000, 2,800,000, 2,850,000, 2,900,000, 2,950,000 or 3,000,000 Da.

In various embodiments, the non-biodegradable body is porous. In some embodiments, the body is 5, 10, 15, 20, 25, 30, 35, 40, 45, 50, 55, 60, 65, 70, 75, 80, 85, 90, 95 or 99% porous. In various embodiments, the pores of the body have a pore size from about 2 to 350 microns. In some embodiments, the pores of the body have a pore size of about 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345 and/or 350 microns.

In some embodiments, the body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

In some embodiments, the material that forms the body has an inherent viscosity (IV) of from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 1 mm to 5 mm and have a diameter of from about 0.01 to about 2 mm. In some embodiments, the drug pellets are 1, 2, 3, 4 and/or 5 mm in size and have a diameter of about 0.01, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95 or about 2 mm. The layer or layers will each have a layer thickness of from about 0.005 to 1.0 mm, such as, for example, from 0.05 to 0.75 mm. In some embodiments, the layer or layers will each have a layer thickness of about 0.005, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95 to 1.0 mm. The drug depot chambers are often larger than the drug depot dimensions to keep the drug depot within the drug chamber.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Retaining Member

In various embodiments, the drug (e.g., drug depot) is stored in the retaining member. In some embodiments, the retaining member comprises one or more channels, each channel capable of storing a plurality of drug depots (e.g., pellets). In some embodiments, the retaining member comprises one or more channels, such as, for example, one channel, two channels, three channels, four channels, five channels or six channels. In various embodiments, each channel is capable of storing and/or holding 6 pellets. In various embodiments, the drug depot is capable of storing and/or holding 1, 2, 3, 4, 5, 6, 7, 8, 9 and/or 10 or more pellets. In some embodiments, each channel is capable of storing and/or holding a single pellet. In various embodiments, the retaining member is cylindrical. In various embodiments, the retaining member is linear and is slidably receivable and is perpendicular to the housing. For example, the retaining member may be a rectangular shape and slide within the within the wall defined by the external surface of the body to engage with the chamber at a position perpendicular to the body.

In some embodiments, the retaining member is monolithic with the body of the drug delivery device. In various embodiments, the retaining member is a separate component from the body of the drug delivery device. In various embodiments, the retaining member ensures retention of the drug depots (e.g., pellets) and prevents un-intentional pellet deployment. For example, in some embodiments, the retaining member is configured to obstruct and/or retain the drug depots (e.g., pellets) from exiting the drug delivery device and is configured to maintain the drug depots within the drug delivering device. In some embodiments, when the drug depots are disposed within the passageway of the chamber, the retaining member acts as an obstruction, preventing the drug depots from deploying from the drug delivery device. In various embodiments, when the drug depots are disposed within the first channel of the retaining member, deployment of the drug depots will not occur until the retaining member is either pushed in a direction and the plunger moves and passes through the first channel or when the retaining member is rotated into a position that allows the plunger to move and pass through the first channel. In some embodiments, the retaining member is automatic or manual.

In various embodiments, the drug delivery device comprises a sating and/or an un-safing mechanism that prevents unintentional deployment of the drug depot (e.g., pellets). In some embodiments, the safing and/or un-safing mechanism is active or passive. In some embodiments, the drug delivery device comprises a safing or un-safing mechanism that is automatic or manual. In some embodiments, active safing includes moving components of the drug delivery device to allow delivery of the drug depot. For example, moving the retaining member to allow the drug depot to be dispensed from the drug delivery device. In some embodiments, passive safing includes movement of the plunger to allow delivery of the drug depot. In various embodiments, the plunger can remove the drug depots from the drug delivery device and/or the retaining member can be contacted and moved by the plunger to remove the drug depots from the drug delivery device for delivery to the target tissue site.

In various embodiments, the plunger contacts by pressing the drug depot and/or the retaining member which causes automatic delivery of the drug depot to the target tissue site.

In various embodiments, the retaining member may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or a combination thereof. In various embodiments, the retaining member is not biodegradable.

In some embodiments, the retaining member comprises a plurality of channels. The channels can be spaced an equal distance from each other. For example, the channels can be spaced 0.5 mm, or 1 mm or 5 mm, or 1 cm to about 2 cm from each other. In the embodiments of the retaining member is not penetrable by the plunger.

In some embodiments, all or a portion of the retaining member can be made from suitable materials including but not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), wax, agar, agarose, gel-vitamin or combinations thereof. In various embodiments, the superior and/or inferior covers comprise poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In various embodiments, the suitable materials can have a molecular weight of about 2,000 Daltons (Da) to about 3,000,000 Da. In some embodiments, the suitable materials have a molecular weight of about 2,000, 5,000, 10,000, 15,000, 20,000, 25,000, 30,000, 35,000, 40,000, 45,000, 50,000, 55,000, 60,000, 65,000, 70,000, 75,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,025,000, 1,050,000, 1,100,000, 1,150,000, 1,200,000, 1,250,000, 1,300,000, 1,350,000, 1,400,000, 1,450,000, 1,500,000, 1,550,000, 1,600,000, 1,650,000, 1,700,000, 1,750,000, 1,800,000, 1,850,000, 1,900,000, 1,950,000, 2,000,000, 2,025,000, 2,050,000, 2,100,000, 2,150,000, 2,200,000, 2,250,000, 2,300,000, 2,350,000, 2,400,000, 2,450,000, 2,500,000, 2,550,000, 2,600,000, 2,650,000, 2,700,000, 2,750,000, 2,800,000, 2,850,000, 2,900,000, 2,950,000 or 3,000,000 Da.

In some embodiments, the suitable materials can have has an inherent viscosity (IV) of from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

The drug device components (e.g., cannula or needle, plunger, retaining member, body, engagement means, etc.) may be lightweight, disposable and sterilizable such that when the device is assembled, the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the drug delivery device provides the advantages of ease of manufacturing in the terminal sterilization process. If the drug pellets are preloaded in the manufacturing process, gamma radiation may be required at higher doses to sterilize the drug depot loaded in the cannula or needle. This is particularly so when the cannula or needle is made from steel or metal. Thus, to sterilize the loaded depot, the dose of gamma rays must be high enough to penetrate the metal, which may destroy the API in the drug depot. By providing a retaining member, for example, made of plastic, the retaining member and drug pellets in the retaining member can be sterilized, without destroying the API and then subsequently loaded by the manufacturer or the user (e.g., surgeon, physician, nurse, etc.). Further, loading the drug depot into the retaining member or cannula is easier. This is particularly so when dealing with multi-dose drug pellets that are relatively small (e.g., 1 mm to 5 mm), the user typically cannot grasp these small pellets and load them into the device. By providing them in a retaining member, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the body, drug cartridge, and/or cannula are transparent so the user can see the position of the plunger and/or the drug depot in the channel of the passageway and/or the retaining member. Thus, indicator markings, in this embodiment, are not needed.

In various embodiments, a kit is provided for delivering a drug pellet to a site beneath the skin of a patient, the kit comprising: a sterilized drug delivery device, comprising: a body comprising a proximal end and a distal end and a chamber disposed therebetween; an upper portion disposed about the proximal end of the body; a retaining member disposed within a wall of the body and engageable with the chamber; and a plunger configured for disposal within the upper portion and the chamber, wherein the upper portion is movable about the proximal end of the body to open the chamber such that the plunger is disposed within a passageway defined within the chamber, and movement of the plunger in a distal direction pushes the retaining member such that the drug moves out of the body.

In various embodiments, a kit is provided which may include additional parts along with the drug depot device combined together to be used to implant the drug depot. The kit may include the drug delivery device in a first compartment. The second compartment may include the any other instruments needed for the implant. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, a method is provided for delivering a drug to a target tissue site, the method comprising: introducing a drug delivery device comprising a body comprising a proximal end and a distal end and a chamber comprising a passageway disposed therebetween, an upper portion disposed about the proximal end of the body that rotates about the proximal end of the body to open the chamber, and a retaining member disposed within a wall of the body and engageable with the chamber; attaching a needle with the distal end of the body; inserting a plunger into the passageway, and moving the plunger in a first position to push the retaining member outward and moving the plunger in a second position such that the drug moves through the needle and is ejected from the delivery device and into the target tissue site.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain, post-operative pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A drug delivery device comprising:
    a body extending along a longitudinal axis between opposite proximal and distal ends, the body comprising opposite inner and outer surfaces, the inner surface defining a passageway;
    a hub rotatably positioned in the passageway;
    a needle coupled to the hub;
    a retaining member coupled to the hub; and
    a sleeve comprising a first wall having an inner surface, the inner surface of the first wall defining a channel, the body being slidably disposed within the channel, the sleeve comprising a second wall coupled to the first wall and a plunger extending from the second wall, the plunger being integrally formed with the first and second walls, the sleeve being configured to translate relative to the body along the longitudinal axis to move the device between a first orientation in which the plunger is spaced apart from the needle and a second orientation in which the plunger is positioned in the needle.

2. The drug delivery device according to claim 1, wherein the body comprises a notch extending into the distal end of the body, the hub being rotatable relative to the body to move the device from a first configuration in which the retaining member is disposed in the notch and a second configuration in which the retaining member is spaced apart from the notch.

3. The drug delivery device according to claim 1, wherein the body includes a vertical wall, the vertical wall including the inner and outer surfaces of the body, the body comprising a transverse wall extending across the proximal end of the body, the trasnsverse wall completely blocking the passageway.

4. The drug delivery device according to claim 1, wherein the proximal end of the body is closed.

5. The drug delivery device according to claim 1, wherein the body includes a tubular wall comprising the inner and outer surfaces of the body, the tubular wall comprising opposite proximal and distal end surfaces, the body comprising spaced apart wings extending distally from the distal end surface.

6. The drug delivery device according to claim 1, wherein the hub comprises a channel, the plunger being spaced apart from the channel of the hub when the device is in the first orientation, the plunger extending through the channel of the hub when the device is in the second orientation.

7. The drug delivery device according to claim 1, wherein the first wall is prevented from directly engaging the hub when the device is in the second orientation.

8. The drug delivery device according to claim 1, wherein the sleeve translates distally relative to the body along the longitudinal axis as the device moves from the first orientation to the second orientation, the hub comprising a channel, the hub rotating relative to the body as the device moves from the first orientation to the second orientation to insert the plunger into the channel of the hub as the device moves from the first orientation to the second orientation.

9. The drug delivery device according to claim 1, wherein the hub rotates relative to the body to insert the plunger into a channel of the hub as the device moves from the first orientation to the second orientation.

10. The drug delivery device according to claim 1, wherein the plunger is spaced apart from a channel of the hub when device is in the first orientation and the hub rotates relative to the body to insert the plunger into the channel of the hub as the device moves from the first orientation to the second orientation.

11. The drug delivery device according to claim 1, wherein: the body includes a tubular wall comprising the inner and outer surfaces of the body, the tubular wall comprising opposite proximal and distal end surfaces, the body comprising spaced apart wings extending distally from the distal end surface, the body a notch extending through the distal end surface, the notch being poisoned between the wings, and the hub is rotatable relative to the body between a first configuration in which the retaining member is positioned within the notch and a second configuration in which the retaining member is spaced apart from the notch.

12. The drug delivery device according to claim 1, wherein:
    the distal end of the body includes spaced apart wings and a notch positioned equidistant between the wings, the hub being rotatable relative to the body between a first configuration in which the retaining member is positioned within the notch and a second configuration in which the retaining member is spaced apart from the notch; and the hub comprises a channel, the plunger being aligned with the channel of the hub when the retaining member is in the second orientation.

13. The drug delivery device according to claim 1, wherein the inner surface of the first wall directly engages the outer surface of the body as the device moves between the first and second orientations.

14. The drug delivery device according to claim 1, wherein the body comprises spaced apart first and second guides extending into the outer surface of the body and the first wall comprises a protrusion extending from the inner surface of the first wall, the protrusion being slidably positioned in one of the first and second guides as the device moves between the first and second orientations.

15. The drug delivery device according to claim 1, wherein at least a portion of the first wall extends 360 degrees about the body.

16. The drug delivery device according to claim 1, wherein the second wall extends from a first section of the first wall to a second section of the first wall.

17. The drug delivery device according to claim 1, wherein the hub comprises a channel, the plunger being aligned with the channel when the retaining member is in the second orientation.

18. The drug delivery device according to claim 17, further comprising a drug depot positioned in the channel of the hub, the plunger being configured to push the drug depot out of the channel of the hub as the device moves from the first orientation to the second orientation.

19. A drug delivery device comprising: a monolithic first member comprising a cylindrical wall extending along a longitudinal axis between opposite proximal and distal end surfaces, the cylindrical wall comprising opposite inner and outer surfaces, the inner surface defining a passageway, the cylindrical wall comprising spaced apart first and second grooves extending into the outer surface, the first member comprising spaced apart wings extending distally from the distal end surface, the cylindrical wall comprising a notch extending into the distal end surface; a monolithic hub rotatably positioned in the passageway; a monolithic needle coupled to the hub; a retaining member coupled to the hub; and a monolithic second member comprising a first wall having an inner surface, the inner surface of the first wall defining a channel, the first wall extending parallel to the longitudinal axis, the second member comprising a protrusion extending from the inner surface of the first wall, the body being slidably disposed within the channel such that the inner surface of the first wall extends 360 degrees about the cylindrical wall and the protrusion is slidably positioned in one of the first and second grooves, the second member comprising a second wall coupled to the first wall and a plunger extending from the second wall, the second wall extending perpendicular to the longitudinal axis, the plunger extending parallel to the longitudinal axis, the second member being configured to translate relative to the first member along the longitudinal axis to move the device between a first orientation in which the plunger is spaced apart from the needle and a second orientation in which the plunger is positioned in the needle, wherein the plunger is spaced apart from a channel of the hub when device is in the first orientation and the hub rotates relative to the first member to insert the plunger into the channel of the hub as the device moves from the first orientation to the second orientation, and wherein the hub is rotatable relative to the first member to move the device from a first configuration in which the retaining member is disposed in the notch and a second configuration in which the retaining member is spaced apart from the notch.

20. A drug delivery device comprising: a monolithic first member comprising a cylindrical wall extending along a longitudinal axis between opposite proximal and distal end surfaces, the cylindrical wall comprising opposite inner and outer surfaces, the inner surface defining a passageway, the cylindrical wall comprising spaced apart first and second grooves extending into the outer surface, the first member comprising spaced apart wings extending distally from the distal end surface, the cylindrical wall comprising a notch extending into the distal end surface; a monolithic hub rotatably positioned in the passageway, the hub comprising a channel; a monolithic needle coupled to the hub, the channel of the hub being in communication with a cannula of the needle; a monolithic retaining member coupled to the hub; a drug depot positioned within the channel of the hub; and a monolithic second member comprising a first wall having an inner surface, the inner surface of the first wall defining a channel, the first wall extending parallel to the longitudinal axis, the second member comprising a protrusion extending from the inner surface of the first wall, the body being slidably disposed within the channel such that the inner surface of the first wall extends 360 degrees about the cylindrical wall and the protrusion is slidably positioned in one of the first and second grooves, the second member comprising a second wall coupled to the first wall and a plunger extending from the second wall, the second wall extending perpendicular to the longitudinal axis, the plunger extending parallel to the longitudinal axis, the second member being configured to translate relative to the first member along the longitudinal axis to move the device between a first orientation in which the plunger is spaced apart from the channel of the hub and the needle and a second orientation in which the plunger is positioned in the needle, wherein the plunger moves the drug depot out of the channel of the hub and through the cannula as the device moves from the first orientation to the second orientation, wherein the plunger is spaced apart from a channel of the hub when device is in the first orientation and the hub rotates relative to the first member to insert the plunger into the channel of the hub as the device moves from the first orientation to the second orientation, and wherein the hub is rotatable relative to the first member to move the device from a first configuration in which the retaining member is disposed in the notch and a second configuration in which the retaining member is spaced apart from the notch.

* * * * *